(12) United States Patent
Cao et al.

(10) Patent No.: US 11,517,212 B2
(45) Date of Patent: Dec. 6, 2022

(54) ELECTROCARDIOGRAM INFORMATION DYNAMIC MONITORING METHOD AND DYNAMIC MONITORING SYSTEM

(71) Applicant: Shanghai Lepu CloudMed Co., Ltd, Shanghai (CN)

(72) Inventors: Jun Cao, Beijing (CN); Chang Liu, Beijing (CN); Weiwei Zhou, Beijing (CN); Hongbo Xin, Beijing (CN); Yan Jiang, Beijing (CN); Zhe Li, Beijing (CN); Liang Tian, Beijing (CN)

(73) Assignee: Shanghai Lepu CloudMed Co., Ltd, Shanghai (CN)

( * ) Notice: Subject to any disclaimer, the term of this patent is extended or adjusted under 35 U.S.C. 154(b) by 76 days.

(21) Appl. No.: 16/766,516

(22) PCT Filed: Apr. 18, 2018

(86) PCT No.: PCT/CN2018/083461
§ 371 (c)(1),
(2) Date: May 22, 2020

(87) PCT Pub. No.: WO2019/161607
PCT Pub. Date: Aug. 29, 2019

(65) Prior Publication Data
US 2021/0369131 A1    Dec. 2, 2021

(30) Foreign Application Priority Data

Feb. 24, 2018   (CN) .......................... 201810157366.8

(51) Int. Cl.
*A61B 5/00*     (2006.01)
*A61B 5/0245*   (2006.01)
(Continued)

(52) U.S. Cl.
CPC ........ *A61B 5/02455* (2013.01); *A61B 5/0006* (2013.01); *A61B 5/308* (2021.01);
(Continued)

(58) Field of Classification Search
CPC ..... A61B 5/02455; A61B 5/332; A61B 5/333; A61B 5/0006; A61B 5/308; A61B 5/35;
(Continued)

(56) References Cited

U.S. PATENT DOCUMENTS

2013/0281816 A1* 10/2013 Strauss .................. G16H 40/67
                                                               600/391
2014/0378851 A1   12/2014 Frei et al.
(Continued)

FOREIGN PATENT DOCUMENTS

CN      205433651 U     8/2016
CN      106821366 A     6/2017
(Continued)

OTHER PUBLICATIONS

European Communication for European Application No. 18907233.3 dated Oct. 14, 2021, 9 pages.
(Continued)

*Primary Examiner* — Scott M. Getzow
(74) *Attorney, Agent, or Firm* — TraskBritt

(57) ABSTRACT

An electrocardiogram information dynamic monitoring method and dynamic monitoring system. The method includes a dynamic monitoring device receiving monitoring reference data input by a user or issued by a server; the data collection on a tested object so as to obtain electrocardiogram data of the tested object; the characteristic identification on the electrocardiogram data so as to obtain characteristic signals of the electrocardiogram data, implementing cardiac activity classification on the electrocardiogram data according to the characteristic signals, obtaining cardiac
(Continued)

activity classification information according to electrocardiogram basic rule reference data, and generating electrocardiogram event data, wherein the electrocardiogram event data comprises device ID information of the dynamic monitoring device; the dynamic monitoring device determining corresponding electrocardiogram event information according to the electrocardiogram event data, and determining whether the electrocardiogram event information is electrocardiogram abnormality event information; and outputting alarm information when the electrocardiogram event information is electrocardiogram abnormality event information.

11 Claims, 9 Drawing Sheets

(51) Int. Cl.
*A61B 5/355* (2021.01)
*A61B 5/35* (2021.01)
*A61B 5/353* (2021.01)
*A61B 5/358* (2021.01)
*A61B 5/308* (2021.01)
*A61B 5/366* (2021.01)

(52) U.S. Cl.
CPC ............... *A61B 5/35* (2021.01); *A61B 5/353* (2021.01); *A61B 5/355* (2021.01); *A61B 5/358* (2021.01); *A61B 5/366* (2021.01); *A61B 5/7221* (2013.01); *A61B 5/7267* (2013.01)

(58) Field of Classification Search
CPC ......... A61B 5/353; A61B 5/355; A61B 5/358; A61B 5/366; A61B 5/7221; A61B 5/7267; A61N 1/3904
See application file for complete search history.

(56) References Cited

U.S. PATENT DOCUMENTS

| | | | |
|---|---|---|---|
| 2016/0183881 A1 | 6/2016 | Keenan et al. | |
| 2017/0087371 A1 | 3/2017 | Freeman et al. | |
| 2017/0296107 A1* | 10/2017 | Reid | A61B 5/4836 |
| 2017/0367599 A1 | 12/2017 | Sanyal et al. | |
| 2018/0242875 A1* | 8/2018 | Volpe | A61B 5/363 |

FOREIGN PATENT DOCUMENTS

| | | |
|---|---|---|
| CN | 107440709 A | 12/2017 |
| CN | 206792389 U | 12/2017 |
| CN | 107714023 A | 2/2018 |
| EP | 2733632 A2 | 5/2014 |
| WO | 00/62664 A1 | 10/2000 |

OTHER PUBLICATIONS

International Search Report for International Application No. PCT/CN2018/083461 dated Nov. 18, 2018, 2 pages.
International Written Opinion for International Application No. PCT/CN2018/083461 dated Nov. 18, 2018, 5 pages.
European Communication pursuant to Article 94(3) EPC for European Application No. 18907233, dated Jul. 1, 2022, 7 pages.

* cited by examiner

ELECTROCARDIOGRAM INFORMATION DYNAMIC MONITORING METHOD AND DYNAMIC MONITORING SYSTEM

CROSS-REFERENCE TO RELATED APPLICATIONS

This application is a national phase entry under 35 U.S.C. § 371 of International Patent Application PCT/CN2018/083461, filed Apr. 18, 2018, designating the United States of America and published as International Patent Publication WO 2019/161607 A1 on Aug. 29, 2019, which claims the benefit under Article 8 of the Patent Cooperation Treaty to Chinese Patent Application Serial No. 201810157366.8, entitled "electrocardiogram information ambulatory monitoring method and ambulatory monitoring system" and filed at National Intellectual Property Administration, PRC on Feb. 24, 2018.

TECHNICAL FIELD

The present disclosure relates to the technical field of data processing, and more particularly, to an electrocardiogram information ambulatory monitoring method and an ambulatory monitoring system.

BACKGROUND

Electrocardiogram monitoring is a common clinical medical monitoring method. The monitored electrocardiogram signals are weak currents reflected by electrical activities of myocardial cells on the body surface, and are recorded by electrodes on the body surface and an amplification recording system.

Comparing with the bedside electrocardiogram monitoring, requirements for non-bedside electrocardiogram monitoring are higher, and it is often easily interfered with by various signals. During the procedure for recording the electrocardiogram signals, other non-cardiac electrical signals, such as myoelectric signal interference caused by skeletal muscle activities, are also recorded. These signals will lead to output of incorrect detection results of heartbeat signals.

The real-time performance of the non-bedside monitoring is also a factor to be considered. Holter, the most commonly used ambulatory electrocardiogram detector, may continuously record the whole process of electrocardiogram activities for 24 hours, including electrocardiogram data under different conditions such as rest, activities, meals, work, study and sleep. However, data analysis and processing are delayed, and may only be known after the monitored person returns Holter to the hospital, which obviously greatly limits the significance and value of the non-bedside monitoring. Holter cannot reflect changes of the electrocardiogram signals of the monitored person in real time like the bedside monitoring, and correspondingly responses in time, especially if the monitored person occurs abnormal and needs medication intervention or rescues.

In addition, the electrocardiogram signals are an embodiment of a process of myocardial electrical activities, which may reflect a large amount of information about a state of the heart. When there is a problem with the state of the heart, the electrocardiogram signals will change accordingly. At present, the accuracy of automatic analysis is far from enough, resulting in that an output electrocardiogram test report does not have a significant reference, and still depends on subjective judgments from doctors.

In order that monitoring has greater significance and plays a greater role, how to effectively improve the level for analyzing the electrocardiogram automatically and realize real-time non-bedside monitoring becomes the difficulty and challenge to be solved by the present disclosure.

BRIEF SUMMARY

The present disclosure provides an electrocardiogram information ambulatory monitoring method and an ambulatory monitoring system, which may realize real-time data interaction through wired or wireless communication technology, timely detect abnormalities and generate alarm information through a complete and rapid automatic analysis of electrocardiogram data, and simultaneously support users to actively report alarms when they are aware of abnormalities. The data is recorded and stored for the cases in which abnormal alarms are generated, so that the reason that causes abnormalities may be quickly analyzed to obtain and it can be traced.

In order to achieve the above purpose, a first aspect of embodiments of the present disclosure provides an electrocardiogram information ambulatory monitoring method, including:

receiving, by an ambulatory monitoring device, monitoring reference data input by a user or distributed by a server; wherein the monitoring reference data includes tested object information and electrocardiogram abnormal event information;

collecting, by the ambulatory monitoring device, monitoring data of the tested object to obtain electrocardiogram data of the tested object;

performing, by the ambulatory monitoring device, waveform feature identification on the electrocardiogram data to obtain feature signals of the electrocardiogram data, performing heartbeat classification on the electrocardiogram data according to the feature signals, obtaining heartbeat classification information with electrocardiogram basic rule reference data and generating electrocardiogram event data; wherein the electrocardiogram event data includes device ID information of the ambulatory monitoring device; and determining, by the ambulatory monitoring device, corresponding electrocardiogram event information according to the electrocardiogram event data, and determining whether the electrocardiogram event information is the electrocardiogram abnormal event information; and outputting alarm information when the electrocardiogram event information is the electrocardiogram abnormal event information.

Preferably, the method further includes:

receiving, by the ambulatory monitoring device, an active alarm instruction input by the tested object;

receiving active alarm information input by the tested object according to the active alarm instruction;

obtaining electrocardiogram data in a preset time period before and after a current time according to the active alarm instruction;

generating active alarm event recording information according to the active alarm instruction and time information at the current time, and generating active alarm event recording data according to the active alarm information and the electrocardiogram data in the preset time period before and after the current time; and sending the active alarm event recording information and the active alarm event recording data to the server.

Preferably, the alarm information includes the electrocardiogram abnormal event information, alarm time information and the device ID information of the ambulatory monitoring device, and the method further includes:

sending, by the ambulatory monitoring device, one or more of the electrocardiogram data, the electrocardiogram event data, alarm information, and abnormal event recording data generated according to a plurality of pieces of electrocardiogram data in a preset time period before and after a time corresponding to the alarm time information to the server.

Further preferably, the method further includes:

receiving and outputting, by the ambulatory monitoring device, alarm feedback information corresponding to the electrocardiogram event data and/or the alarm information sent by the server.

Further preferably, the performing waveform feature identification on the electrocardiogram data to obtain feature signals of the electrocardiogram data, performing heartbeat classification on the electrocardiogram data according to the feature signals, obtaining heartbeat classification information with electrocardiogram basic rule reference data and generating electrocardiogram event data, includes:

converting a data format of the electrocardiogram data into a preset standard data format by resampling, and performing a first filtering processing on converted electrocardiogram data in the preset standard data format;

performing heartbeat detection processing on electrocardiogram data processed by the first filtering processing to identify a plurality of pieces of heartbeat data included in the electrocardiogram data, each of which corresponds to a heartbeat cycle, including amplitude and starting-ending time data of corresponding P wave, QRS complex and T wave;

determining a detection confidence level of each heartbeat according to the heartbeat data;

performing interference identification on the heartbeat data according to an two-class interference identification model to obtain whether there is interference noise in the heartbeat data with a probability value for judging the interference noise;

determining a validity of the heartbeat data according to the detection confidence level, and, according to lead parameters of determined valid heartbeat data and the heartbeat data, combining and generating heartbeat time sequence data based on results of the interference identification and time rules; and generating heartbeat analysis data according to the heartbeat time sequence data;

performing feature extraction and analysis of an amplitude and time characterization data on the heartbeat analysis data according to a heartbeat classification model, to obtain primary classification information of the heartbeat analysis data;

inputting the heartbeat analysis data of particular heartbeats in results of the primary classification information into a ST segment and T wave change model for identification, and determining ST segment and T wave evaluation information;

performing P wave and T wave feature detection on the heartbeat analysis data according to the heartbeat time sequence data to determine detailed feature information of the P wave and the T wave in each heartbeat, wherein the detailed feature information includes data of amplitudes, directions, forms and starting-ending time;

performing secondary classification processing on the heartbeat analysis data according to the electrocardiogram basic rule reference data, the detailed feature information of the P wave and the T wave and the ST segment and T wave evaluation information under the primary classification information to obtain heartbeat classification information; and analyzing and matching the heartbeat classification information to generate the electrocardiogram event data.

The electrocardiogram information ambulatory monitoring method according to the first embodiment of the present disclosure performs complete and rapid automatic analysis of the electrocardiogram data through the ambulatory monitoring device, detects abnormalities in time and generates the alarm information, and simultaneously supports the users to actively report alarms when they are aware of abnormalities. The data is recorded and stored for the cases in which abnormal alarms are generated, so that the reason that causes abnormalities may be quickly analyzed to obtain and it can be traced.

A second aspect of embodiments of the present disclosure provides another electrocardiogram information ambulatory monitoring method, including:

collecting, by an ambulatory monitoring device, physical sign monitoring data of a tested object to obtain electrocardiogram data of the tested object, obtaining tested object information, and sending the electrocardiogram data and the tested object information to a server; wherein the electrocardiogram data has time attribute information and device ID information of the ambulatory monitoring device;

performing, by the server, waveform feature identification on the electrocardiogram data to obtain feature signals of the electrocardiogram data, performing heartbeat classification on the electrocardiogram data according to the feature signals, obtaining heartbeat classification information with electrocardiogram basic rule reference data and generating electrocardiogram event data; wherein the electrocardiogram event data includes the device ID information of the ambulatory monitoring device;

determining, by the server, monitoring reference data according to the tested object information; wherein the monitoring reference data includes electrocardiogram abnormal event information corresponding to the tested object information;

determining, by the server, corresponding electrocardiogram event information according to the electrocardiogram event data, and determining whether the electrocardiogram event information is electrocardiogram abnormal event information; and generating alarm information if the electrocardiogram event information is electrocardiogram abnormal event information; wherein the alarm information includes the electrocardiogram abnormal event information, alarm time information and the device ID information of the ambulatory monitoring device; and sending, by the server, the alarm information to the ambulatory monitoring device according to the device ID information of the ambulatory monitoring device, so that the ambulatory monitoring device generates a corresponding alarm output signal according to the alarm information.

Preferably, the method further includes:

receiving, by the ambulatory monitoring device, an active alarm instruction input by the tested object;

receiving active alarm information input by the tested object according to the active alarm instruction;

obtaining electrocardiogram data in a preset time period before and after a current time according to the active alarm instruction;

generating active alarm event recording information according to the active alarm instruction and time information at the current time, and generating active alarm event recording data according to the active alarm information and the electrocardiogram data in the preset time period before and after the current time; and sending the active alarm event recording information and the active alarm event recording data to the server.

Preferably, the method further includes:

if the electrocardiogram event information is electrocardiogram abnormal event information, obtaining, by the server, a plurality of pieces of electrocardiogram data in a preset time period before and after a time corresponding to the electrocardiogram data according to the time attribute information, and generating abnormal event recording data; and generating, by the server, relationship information between the abnormal event recording data and the alarm information.

Preferably, the performing waveform feature identification on the electrocardiogram data to obtain feature signals of the electrocardiogram data, performing heartbeat classification on the electrocardiogram data according to the feature signals, obtaining heartbeat classification information in combination with electrocardiogram basic rule reference data and generating electrocardiogram event data, includes:

converting a data format of the electrocardiogram data into a preset standard data format by resampling, and performing a first filtering processing on converted electrocardiogram data in the preset standard data format;

performing heartbeat detection processing on electrocardiogram data processed by the first filtering processing to identify a plurality of pieces of heartbeat data included in the electrocardiogram data, each of which corresponds to a heartbeat cycle, including amplitude and starting-ending time data of corresponding P wave, QRS complex and T wave;

determining a detection confidence level of each heartbeat according to the heartbeat data;

performing interference identification on the heartbeat data according to a two-class interference identification model to obtain whether there is interference noise in the heartbeat data with a probability value for judging the interference noise;

determining a validity of the heartbeat data according to the detection confidence level, and, according to lead parameters of determined valid heartbeat data and the heartbeat data, combining and generating heartbeat time sequence data based on results of the interference identification and time rules; and generating heartbeat analysis data according to the heartbeat time sequence data;

performing feature extraction and analysis of an amplitude and time characterization data on the heartbeat analysis data according to a heartbeat classification model, to obtain primary classification information of the heartbeat analysis data;

inputting the heartbeat analysis data of particular heartbeats in results of the primary classification information into a ST segment and T wave change model for identification, and determining ST segment and T wave evaluation information;

performing P wave and T wave feature detection on the heartbeat analysis data according to the heartbeat time sequence data to determine detailed feature information of the P wave and the T wave in each heartbeat, wherein the detailed feature information includes data of amplitudes, directions, forms and starting-ending time;

performing secondary classification processing on the heartbeat analysis data according to the electrocardiogram basic rule reference data, the detailed feature information of the P wave and the T wave and the ST segment and T wave evaluation information under the primary classification information to obtain heartbeat classification information; and analyzing and matching the heartbeat classification information to generate the electrocardiogram event data.

The electrocardiogram information ambulatory monitoring method according to the second embodiment of the present disclosure collects the electrocardiogram data through the ambulatory monitoring device, uploads the electrocardiogram data to the server for complete and rapid automatic analysis, timely detect abnormalities, generates the alarm information and sends the same to the ambulatory monitoring device, and meanwhile, the ambulatory monitoring device supports users to actively report the alarm if they are aware of abnormalities. The server records and stores the data for the cases in which abnormal alarms are generated, so that the reason that causes abnormalities may be quickly analyzed to obtain and it can be traced.

A third aspect of embodiments of the present disclosure provides an ambulatory monitoring system, including one or more ambulatory monitoring devices and the server according to the first aspect; the ambulatory monitoring devices include a memory used for storing programs and a processor used for executing the first aspect and the methods in implementation manners of the first aspect.

A fourth aspect of embodiments of the present disclosure provides a computer program product including instructions, when the computer program product runs on a computer, the computer executes the first aspect and the methods in implementation manners of the first aspect.

A fifth aspect of embodiments of the present disclosure provides a computer readable storage medium storing computer programs, when the computer programs are executed by a processor, the first aspect and the methods in implementation manners of the first aspect are realized.

A sixth aspect of embodiments of the present disclosure provides an ambulatory monitoring system, including the server and one or more ambulatory monitoring devices according to the second aspect; the server includes a memory used for storing programs and a processor used for executing the methods in implementation manners of the second aspect and the first aspect.

A seventh aspect of embodiments of the present disclosure provides a computer program product including instructions, when the computer program product runs on a computer, the computer executes the second aspect and the methods in implementation manners of the second aspect.

An eighth aspect of embodiments of the present disclosure provides a computer readable storage medium storing computer programs, when the computer programs are executed by a processor, the second aspect and the methods in implementation manners of the second aspect are realized.

DETAILED DESCRIPTION

Technical solutions of the present disclosure will be further described in detail below through accompanying drawings and embodiments.

Ambulatory electrocardiogram is a method that may continuously record, compile and analyze electrocardiogram changes of human heart in activities or in rest for a long time, which has become one of important diagnostic methods for non-invasive examination in clinical cardiovascular field. Compared with ordinary electrocardiogram, the ambulatory electrocardiogram may continuously record up to 100,000 electrocardiogram signals within 24 hours, which may improve a detection rate of non-persistent arrhythmia, especially transient arrhythmia and transient myocardial ischemic attack. More than 90% of heart disease outbreaks occur outside of medical institutions, so it is very necessary for people with a history of heart disease to record and monitor their daily heart conditions.

Therefore, the present disclosure provides an electrocardiogram information ambulatory monitoring method, which may be applied to an ambulatory monitoring system consisting of wearable ambulatory monitoring devices and a server, realizes real-time data interaction through wired or wireless communication technology, timely discovers abnormalities and generates alarm information through complete and rapid automatic analysis of electrocardiogram data, and simultaneously supports users to actively report alarms when they are aware of abnormalities. The data is recorded and stored for the cases in which abnormal alarms are generated, so that the reason that causes abnormalities may be quickly analyzed to obtain and it can be traced.

This method may be mainly performed in the ambulatory monitoring devices, or in the server. The ambulatory monitoring devices mainly perform collecting electrocardiogram data, and interacting and outputting of the alarm information. The two different cases are described below with the following two embodiments.

Figure 1:
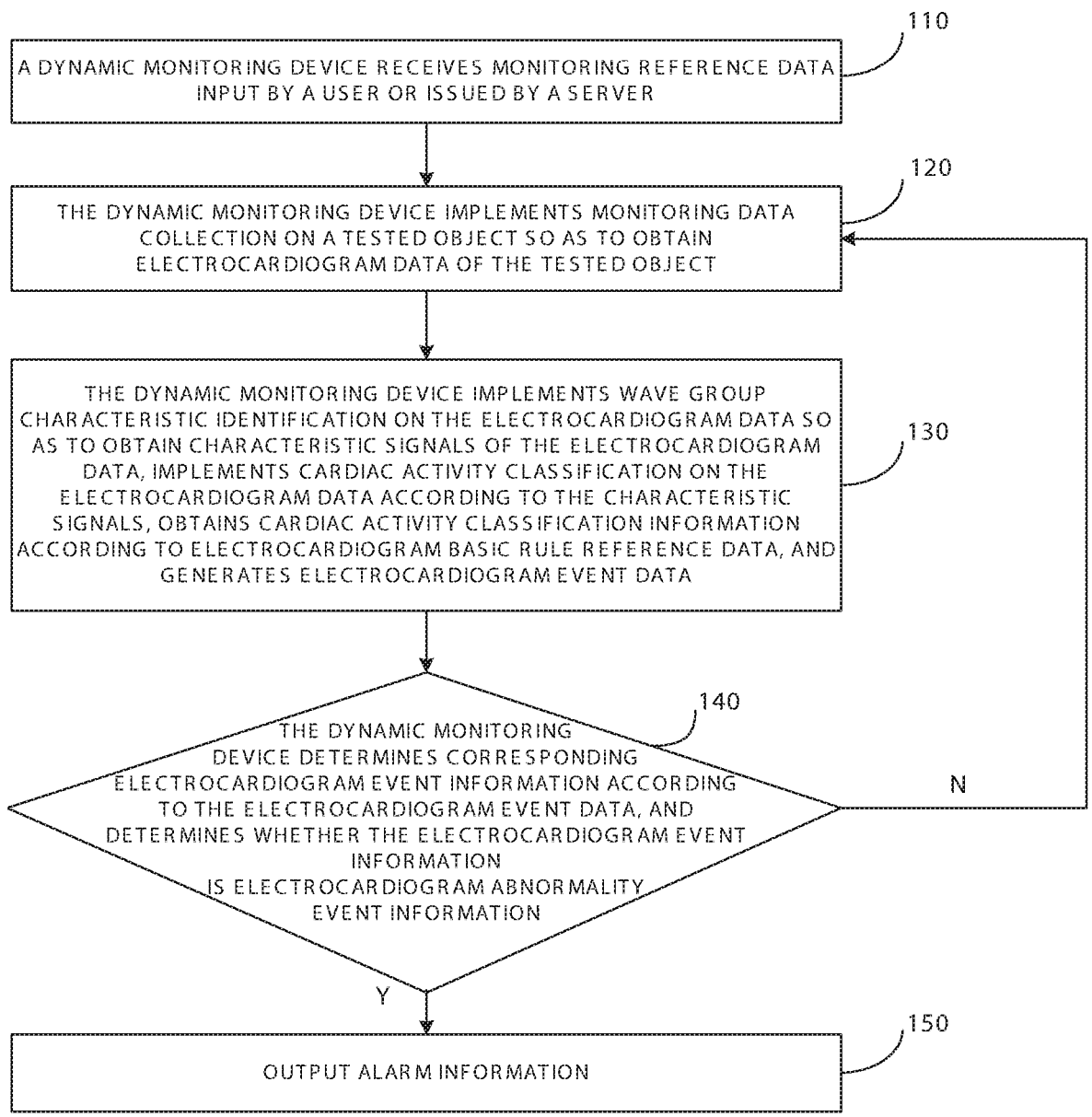
FIG. 1 is a flowchart illustrating an electrocardiogram information ambulatory monitoring method according to an embodiment of the present disclosure.

The electrocardiogram information ambulatory monitoring method according to the present disclosure will be described in detail below with reference to the flowchart of the electrocardiogram information ambulatory monitoring method shown in FIG. 1. In this embodiment, the electrocardiogram information ambulatory monitoring method is mainly performed in the ambulatory monitoring device. As shown in FIG. 1, the electrocardiogram information ambulatory monitoring method according to the present disclosure includes the following steps:

Step 110, the ambulatory monitoring device receives monitoring reference data input by the user or issued by the server.

The ambulatory monitoring device may be a single-lead or multi-lead wearable electrocardiogram monitor, and each ambulatory monitoring device has a unique device Identification (ID). When the ambulatory monitoring device is assigned to a user to be monitored, corresponding monitoring reference data may be configured in the ambulatory monitoring device according to the situation of the user.

The monitoring reference data may be understood as reference data or information indicating whether the monitored electrocardiogram signal of the user is normal or not and whether an alarm needs to be generated. The monitoring reference data may be set different for different users. Specifically, the monitoring reference data may be obtained by configuring a manner for inputting it on the ambulatory monitoring device or by configuring it according to user information and distributing it to the ambulatory monitoring device through the server.

In this embodiment, the monitoring reference data may include tested object information and configured electrocardiogram abnormal event information. The electrocardiogram abnormal event information includes information of various electrocardiogram abnormal events that need to be generated electrocardiogram abnormal alarms. When the ambulatory monitoring device obtains the electrocardiogram abnormal event indicated by the electrocardiogram data by means of performing a series of processing such as collecting and analyzing the electrocardiogram data, whether an alarm is generated may be determined by determining whether the electrocardiogram abnormal event is an event specified in the electrocardiogram abnormal event information.

Step 120, the ambulatory monitoring device collects monitoring data of the tested object to obtain the electrocardiogram data of the tested object.

The ambulatory monitoring device collects and records signals generated by electrophysiological activities of heart cells in a single-lead or multi-lead form through non-invasive electrocardiogram examination to obtain the electrocardiogram data. The electrocardiogram data includes the ID of the tested object, the device ID of the ambulatory monitoring device and detection time information.

Step 130, the ambulatory monitoring device performs waveform feature identification on the electrocardiogram data to obtain feature signals of the electrocardiogram data, performs heartbeat classification on the electrocardiogram data according to the feature signals, obtains heartbeat classification information with electrocardiogram basic rule reference data and generates electrocardiogram event data.

Considering that other non-cardiogenic electrical signals, such as myoelectric signal interference caused by skeletal muscle activities, are also recorded during the procedure for ambulatory monitoring and recording the electrocardiogram signals, it is thought that effective interference identification and elimination on the electrocardiogram signals are needed to effectively reduce false positives caused by interference signals.

In addition, the electrocardiogram signals are an embodiment of a process of myocardial electrical activities, so in addition to being used to detect heart rate, the electrocardiogram signals may also reflect a large amount of information about the state of the heart. When there is a problem with the heart state, the electrocardiogram signals will change accordingly. In the research on existing processing methods of the electrocardiogram signals in the industry, it found that only very limited analysis and alarm have been carried out on the electrocardiogram signals at present. In addition to effective interference identification and elimination on the electrocardiogram signals to reduce false positives caused by the interference signals, it is thought that improvements may be made from the following points:

First, an accurate identification of P wave and T wave should be required during feature extraction of heartbeats, which may avoid excessive detection and missed detection in heartbeat detection, for example, excessive detection of some special electrocardiogram signals, such as tall T waves of patients with slow heart rhythm or signals with hypertrophy of T wave quickly and effectively.

Second, the heartbeats should be categorized into more detailed classes, and it cannot only be classified in three types including sinus, supraventricular and ventricular, so as to meet complicated and comprehensive analysis requirements of clinical electrocardiogram doctors.

Third, atrial flutter, atrial fibrillation and ST-T changes should be correctly identified, which are helpful to the analysis of myocardial ischemia with the assistance of ST segment and T wave changes.

Fourth, the heartbeats and electrocardiogram events should be accurately identified.

In the present disclosure, aiming at the above points, the electrocardiogram data are analyzed and calculated, especially in the case of the introduction of artificial intelligence (AI) technology, arrhythmia analysis long intermittent arrest, flutter and fibrillation, conduction block, premature beat and escape beat, bradycardia, tachycardia, ST segment change detection are performed on the collected digital signals, and analysis and classification are performed on the electrocardiogram events, so that it is achieved that accurate alarm signals are generated to effectively monitor vital signs of patients.

Based on the above points, the processing procedure of the electrocardiogram data of the present disclosure adopts an artificial intelligence self-learning-based electrocardiogram automatic analysis method and is realized based on an artificial intelligence Convolutional Neural Network (CNN) model. The CNN model is a supervised learning method in deep learning, which is a multi-layer network (hidden layer) connection structure that simulates a neural network. An input signal sequentially passes through each hidden layer, in which a series of complex mathematical processes (Convolution, Pooling, Regularization, prevention of over-fitting, Dropout, Activation, and general use of Rectified Linear Unit activation function) are carried out. Some features of an object to be identified are automatically abstracted layer by layer, these features are transmitted as input to the higher hidden layers and the last several full connection layers for calculation, and Softmax function is used to perform logistics regression to achieve multi-objective classification.

CNN belongs to the supervised learning method in artificial intelligence. In a training phase, the input signal is processed through multiple hidden layers to reach last full connection layers. There is an error between a classification result obtained by Softmax logical regression and a known classification result (label). One of core ideas of deep learning is to continuously minimize the error through a large number of sample iterations so as to calculate and obtain parameters for connecting neurons in each hidden layer. In this process, it is generally necessary to construct a special cost function, and quickly and effectively updating all connection parameters in a neural network structure with complex depth (number of hidden layers) and breadth (dimension of features) by using a nonlinearly optimized gradient descent algorithm and an error back propagation (BP) algorithm.

In deep learning, data needed to be identified is input into a training model, and finally an identification result is output after the data passes through all layers of the network.

In the present disclosure, wave complex feature identification, interference identification, heartbeat classification and the like performed on the electrocardiogram data are all based on trained models based on artificial intelligence self-learning to obtain output results, with a fast analysis speed and a high accuracy.

Figure 2:
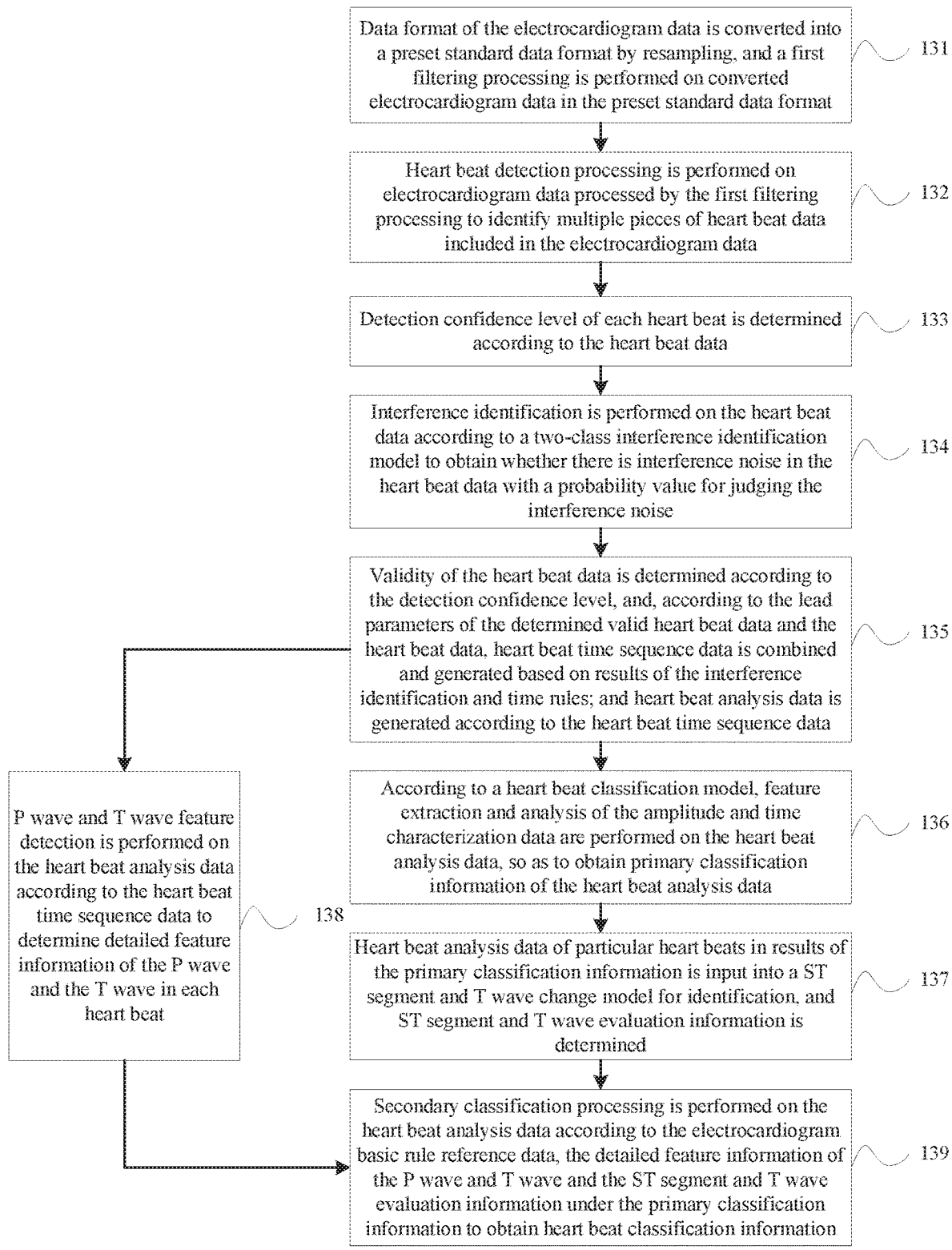
FIG. 2 is a flowchart illustrating a method for processing electrocardiogram data according to an embodiment of the present disclosure.

Described in more detailed, this step is realized through obtaining feature signals of the electrocardiogram data by performing wave complex feature identification on the electrocardiogram data, classifying the electrocardiogram data according to the feature signals, obtaining heartbeat classification information with electrocardiogram basic rule reference data, generating electrocardiogram event data according to the heartbeat classification information, and finally generating the report data. Further, the process may be specifically implemented by the following steps shown in FIG. 2.

Step 131, a data format of the electrocardiogram data is converted into a preset standard data format by resampling, and a first filtering processing is performed on converted electrocardiogram data in the preset standard data format.

The format of the electrocardiogram data is adapted to read, and different readings are implemented for different devices. A baseline needs to be adjusted and the electrocardiogram data needs to be converted into millivolt data according to a gain after reading. Through data resampling, the data is converted into data at a sample frequency that may be processed by the whole process. Then, high frequency, low-frequency noise interference and baseline drift are eliminated by filtering to improve the accuracy of artificial intelligence analysis. Processed electrocardiogram data is stored in the preset standard data format.

Through this step, differences in the lead, sample frequency and transmission data format used by different electrocardiogram devices may be eliminated, and the high frequency, low-frequency noise interference and baseline drift may be removed by digital signal filtering.

The digital signal filtering may adopt a high-pass filter, low-pass filter and median filtering respectively to eliminate power line interferences, electromyogram interferences and baseline drift interferences, so as to avoid the impact on subsequent analysis.

More specifically, a low-pass, high-pass Butterworth filter may be used for zero-phase shift filtering to eliminate the baseline drift and high-frequency noise interference, and to retain effective electrocardiogram signals. The median filtering may replace an amplitude of a sequence in a center of a window with a median of voltage amplitudes of data points in a sliding window of a preset length of time, and a low-frequency baseline drift may be eliminated.

Step 132, heartbeat detection processing is performed on electrocardiogram data processed by the first filtering to identify multiple pieces of heartbeat data included in the electrocardiogram data.

Each of the multiple pieces of heartbeat data corresponds to a heartbeat cycle, including amplitudes and starting-ending time data of corresponding P wave, QRS complex and T wave. The heartbeat detection in this step includes two processes: one is signal processing, extracting characteristic frequency bands of the QRS complex from the electrocardiogram data processed by the first filtering processing, and the other is to determine occurrence time of the QRS complex by setting a reasonable threshold. The electrocardiogram normally includes components of P wave, QRS complex and T wave, and a noise component. Generally, the QRS complex has a frequency range from 5 Hz to 20 Hz, so signals of the QRS complex may be extracted by a band-pass filter in this range. However, frequency bands of the P wave, the T wave, and the noise are partially overlapped with the QRS complex, so signals of non QRS complex may not be completely removed by the signal processing. Therefore, it is necessary to extract a position of the QRS complex from a signal envelope by setting a reasonable threshold. The specific detection process is a process based on peak detection. Threshold judgment is sequentially performed for each peak in the signals, and when the threshold is exceeded, a judgment process of the QRS complex is implemented to detect more features, such as RR interval, morphology, etc.

During the recording process of the electrocardiogram information, the amplitude and frequency of heartbeat signals constantly change, and this characteristic is stronger in a disease state. When the threshold is set, a threshold adjustment needs to be dynamically performed according to the change of data characteristics in the time domain. In order to improve the accuracy and positive rate of the detection, the QRS complex detection is mostly carried out by a double amplitude threshold combined with a time threshold. A high threshold has a high positive rate and a low threshold has a high sensitivity rate. When the RR interval exceeds a certain time threshold, the low threshold is used for detection to reduce missed detection. However, the low threshold is susceptible to T wave and electromyography noise due to its low threshold, which is easy to cause excessive detection. Therefore, the high threshold is preferred for detection.

For heartbeat data of different leads, there are lead parameters to characterize which lead the heartbeat data belongs to. Therefore, when the electrocardiogram data is obtained, the information of the lead that the data belongs to may be determined according to a transmission source, and the information is taken as the lead parameters of the heartbeat data.

Step 133, a detection confidence level of each heartbeat is determined according to the heartbeat data.

During the process of the heartbeat detection, a confidence calculation module may provide an estimation value of the detection confidence level for the QRS complex according to an amplitude of the QRS complex and an amplitude ratio of noise signals within the RR interval.

Step 134, interference identification is performed on the heartbeat data according to a two-class interference identification model to obtain whether there is interference noise in the heartbeat data with a probability value for judging the interference noise.

The long-time recording process is susceptible to interference caused by various influences, resulting in invalid or inaccurate acquired heartbeat data, which cannot correctly reflect condition of participants and increases the difficulty and workload of doctors in diagnosis. In addition, interference data is also a main factor that causes intelligent analysis tools unable to work effectively. Therefore, it is particularly important to minimize external signal interference.

This step is based on an end-to-end two-class identification model with deep learning algorithms as its core, and it has characteristics of high precision and strong generalization performance, and may effectively solve disturbance problems caused by main disturbance sources such as electrode peeling off, exercise interference and electrostatic interference, and thus, the problem of poor identification effect caused by various and irregular disturbance data in traditional algorithms is overcome.

It may be achieved through the following method:
step A: using the two-class interference identification model for the heartbeat data to identify interference;
step B: identifying a data segment with a heartbeat interval greater than or equal to a preset interval determination threshold in the heartbeat data;
step C: performing a judgment of signal abnormality on the data segment with the heartbeat interval greater than or equal to the preset interval determination threshold to determine whether the data segment is an abnormal signal;
wherein the identification of the abnormal signal includes whether there are electrode peeling off, low voltage, etc.
step D: if the data segment is not an abnormal signal, according to a set time value, a starting data point and an ending data point of sliding sampling in the data segment are determined with a preset time width, and the sliding sampling is performed on the data segment from the starting data point until the ending data point to obtain multiple sample data segments; and
step E: performing the process for interference identification on each of the multiple sample data segments.

The above steps A-E will be described in an exemplary example. The heartbeat data of each lead is cut and sampled with a set first data amount, and then input into the two-class interference identification model respectively for classification, and an interference identification result and a probability value corresponding to such result are obtained. For the heartbeat data with the heartbeat interval greater than or equal to 2 seconds, whether it is signal overflow, low voltage, electrode peeling off is first judged. If it is not in the above case, sliding sampling without overlapping is continuously performed from a left heartbeat to the right with the first data amount for identification.

The input may be the first data amount of heartbeat data of any lead, the two-class interference identification model is adopted for classification, and a classification result of whether the heartbeat data is the interference or not is directly output. The result is obtained quickly, the accuracy is high, the stability performance is good, and effective and high-quality data may be provided for subsequent analysis.

Interference data is often caused by external disturbance factors, mainly including electrode peeling off, low voltage, electrostatic interference and motion interference. Not only interference data generated by different disturbance sources is different, but also interference data generated by a same disturbance source is diverse. At the same time, considering that although the diversity of interference data is widely distributed, the difference with normal data is very large, so the diversity is ensured as much as possible when collecting interference training data. Furthermore, moving window sliding sampling is adopted to increase the diversity of interference data as much as possible, so as to make the model robust to interference data. Even if interference data in the future is different from any previous interference, with comparison to normal data, its similarity with interference is greater than normal data, thus enhancing the ability of the model to identify interference data.

Figure 3:
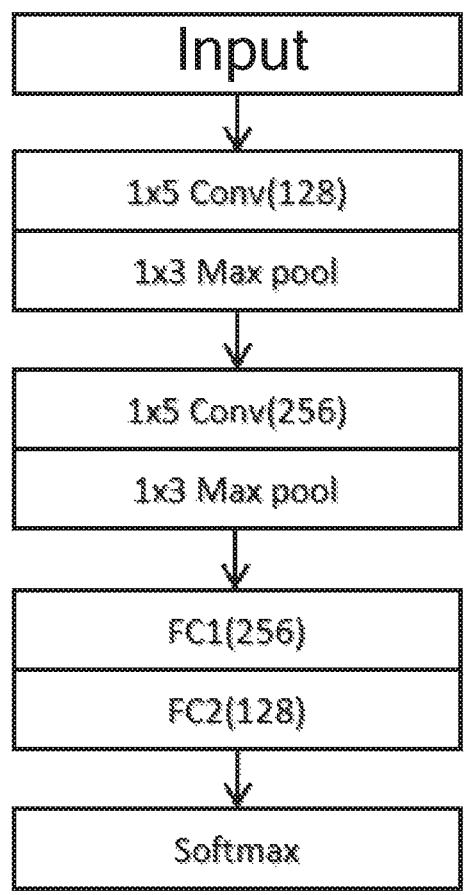
FIG. 3 is a schematic diagram illustrating a two-class interference identification model according to an embodiment of the present disclosure.

The two-class interference identification model adopted in this step may be shown in FIG. 3. The network first uses two convolutional layers, the convolution kernel in size is 1×5, and each layer is followed by a maximum pooling. The number of the convolution kernel starts from 128, and the number of the convolution kernel doubles every time passing a maximum pooling layer. The convolutional layers are followed by two full connection layers and a Softmax classifier. Since the classification number of the model is two, Softmax has two output units which correspond to corresponding categories in turn, and uses cross entropy as the cost function.

For the training of the model, nearly 4 million accurately labeled data segments from 300,000 patients are used. Labeling is divided into two categories: normal electrocardiogram signals or electrocardiogram signal fragments with obvious interference. The segments are labeled by custom-developed tools, and then interference fragment information is saved in a customized standard data format.

In the training process, two GPU servers are used for dozens of round-robin training. In a specific example, for a segment D [300] with a sample rate of 200 Hz and a data length of 300 electrocardiogram voltage values (millivolts), input data is: InputData (i, j), wherein i is an i-th lead, and j is a j-th segment of the i-th lead. All input data is randomly scattered before training, which ensures convergence of the training process. At the same time, collection of too many samples from the electrocardiogram data of a same patient is controlled, improving the generalization ability of the model, that is, an accuracy rate in a real scene. After the training converges, one million pieces of independent test data are used for testing, and the accuracy rate may reach 99.3%. Additionally, specific test data is shown in Table 1 below.

TABLE 1

|  | Interference | Normal |
| --- | --- | --- |
| Sensitivity | 99.14% | 99.32% |
| Positive Predictivity | 96.44% | 99.84% |

Step 135, a validity of the heartbeat data is determined according to the detection confidence level, and, according to the lead parameters of the determined valid heartbeat data and the heartbeat data, heartbeat time sequence data is combined and generated based on results of the interference identification and time rules; and heartbeat analysis data is generated according to the heartbeat time sequence data.

Specifically, due to the complexity of the electrocardiogram signals and the fact that each lead may be affected by different degrees of interference, there may be excessive detection and missed detection when the heartbeat detection depends on a single lead. Time characterization data of heartbeat results detected by different leads is not aligned. Therefore, the heartbeat data of all leads needs to be combined according to results of the interference identification and time rules to generate complete heartbeat time sequence data, and the time characterization data of the heartbeat data of all leads is unified. The time characterization data is used to represent time information of each data point on a time axis of electrocardiogram data signals. In the subsequent analysis and calculation, according to the unified heartbeat time sequence data, the heartbeat data of each lead may be cut with the preset threshold, so as to generate the heartbeat analysis data of each lead required for specific analysis.

Before the above mentioned heartbeat data of each lead is combined, the validity of the heartbeat data needs to be determined according to the detection confidence level obtained in step 133.

Specifically, the process of combining the heartbeat data performed by the lead heartbeat combination module is as follows: a time characterization data combination of the heartbeat data of different leads is obtained according to a refractory period of electrocardiogram basic rule reference data, the heartbeat data with a large deviation is discarded, the time characterization data combination is voted to generate a position of a combined heartbeat, and the position of the combined heartbeat is added to the combined heartbeat time sequence. It returns to a next group of heartbeat data to be processed, and repeats until combination of all heartbeat data is finished.

The refractory period of the electrocardiogram activities may preferably be between 200 ms and 280 ms. The time characterization data combination of the heartbeat data of different leads obtained should meet the following conditions: each lead in the time characterization data combination of the heartbeat data includes at most the time characterization data of one piece of heartbeat data. When the time characterization data combination of the heartbeat data is voted on, it is determined by a percentage of a number of leads with detected heartbeat data in a number of effective leads. If a position of the time characterization data of the heartbeat data corresponding to a lead is a low voltage segment, an interference segment or electrode peeling off, the lead is considered as an invalid lead for the heartbeat data. The specific position of the combined heartbeat may be calculated and obtained by using an average value of the time characterization data of the heartbeat data. During the combining process, the refractory period is set in this method to avoid erroneous combining.

In this step, the unified heartbeat time sequence data is output through combining. This step may simultaneously lower excessive detection and missed detection rates of the heartbeat, and effectively improve the sensitivity and positive predictivity of the heartbeat detection.

Step 136, according to a heartbeat classification model, feature extraction and analysis of the amplitude and time characterization data are performed on the heartbeat analysis data, so as to obtain primary classification information of the heartbeat analysis data.

Since there are differences in signal measurement, acquisition, output lead data and other aspects for different electrocardiogram monitoring devices, a simple single-lead classification method or a multi-lead classification method may be adopted according to specific situations. The multi-lead classification method includes lead voting decision classification method and lead synchronous correlation classification method. The lead voting decision classification method is a voting decision method that leads are independently classified based on the heartbeat analysis data of each lead, and then voting results are merged to determine a classification result. The lead synchronous correlation classification method is a method for synchronous correlation and analysis of the heartbeat analysis data of each lead. The single-lead classification method is to directly use a corresponding lead model to classify the heartbeat analysis data of a single-lead device, and there is no voting decision process. The classification methods mentioned-above will be respectively described in the following.

The single-lead classification method includes:
according to the heartbeat time sequence data, cutting is performed on the heartbeat data of the single lead to generate the heartbeat analysis data of the single lead, and the heartbeat analysis data of the single lead is input into the trained heartbeat classification model corresponding to such lead for the feature extraction and analysis of the amplitude and time characterization data, so as to obtain the primary classification information of the single lead.

The lead voting decision classification method may include:
firstly, according to the heartbeat time sequence data, cutting is performed on the heartbeat data of each lead to generate the heartbeat analysis data of each lead;
secondly, according to the trained heartbeat classification model corresponding to each lead, the feature extraction and analysis of the amplitude and time characterization data are performed on the heartbeat analysis data of each lead, so as to obtain classification information of each lead; and
thirdly, classification voting decision calculation is performed according to the classification information of each lead and lead weight reference coefficients, so as to obtain the primary classification information. Specifically, the lead weight reference coefficients are voting weight coefficients of each lead for different heartbeat classifications based on the Bayesian statistical analysis of the electrocardiogram data.

The lead synchronous correlation classification method may include:
according to the heartbeat time sequence data, cutting is performed on the heartbeat data of each lead to generate the heartbeat analysis data of each lead; and then, according to a trained multi-lead synchronous correlation classification model, the feature extraction and analysis of a synchronous amplitude and time characterization data are performed on the heartbeat analysis data of each lead, so as to obtain the primary classification information of the heartbeat analysis data.

An input of the synchronous correlation classification method of the heartbeat data is data of all leads of the ambulatory electrocardiogram device, and data points with a same position and a certain length of each lead are intercepted according to unified heartbeat positions of the heartbeat analysis data, and are synchronously delivered to a trained artificial intelligence deep learning model for calculation and analysis, and an output is that an accurate heartbeat classification in which electrocardiogram signal characteristics of all lead and heart rhythm characteristics correlated with the heartbeat in time are comprehensively considered at each heartbeat position.

In this method, it is fully considered the data of different leads of the electrocardiogram is, actually measuring information flow of heart electrical signals transmitted in the directions of different electrocardiogram axis vectors, and multi-dimensional digital characteristics transmitted by the electrocardiogram signal in time and space are comprehensively analyzed, so it effectively overcomes the defect that the traditional method only relies on independent analyses of a single lead, and then results are accumulated to conduct some statistical voting methods through which classification errors are easily obtained, and greatly improves the accuracy of the heartbeat classification.

Figure 4:
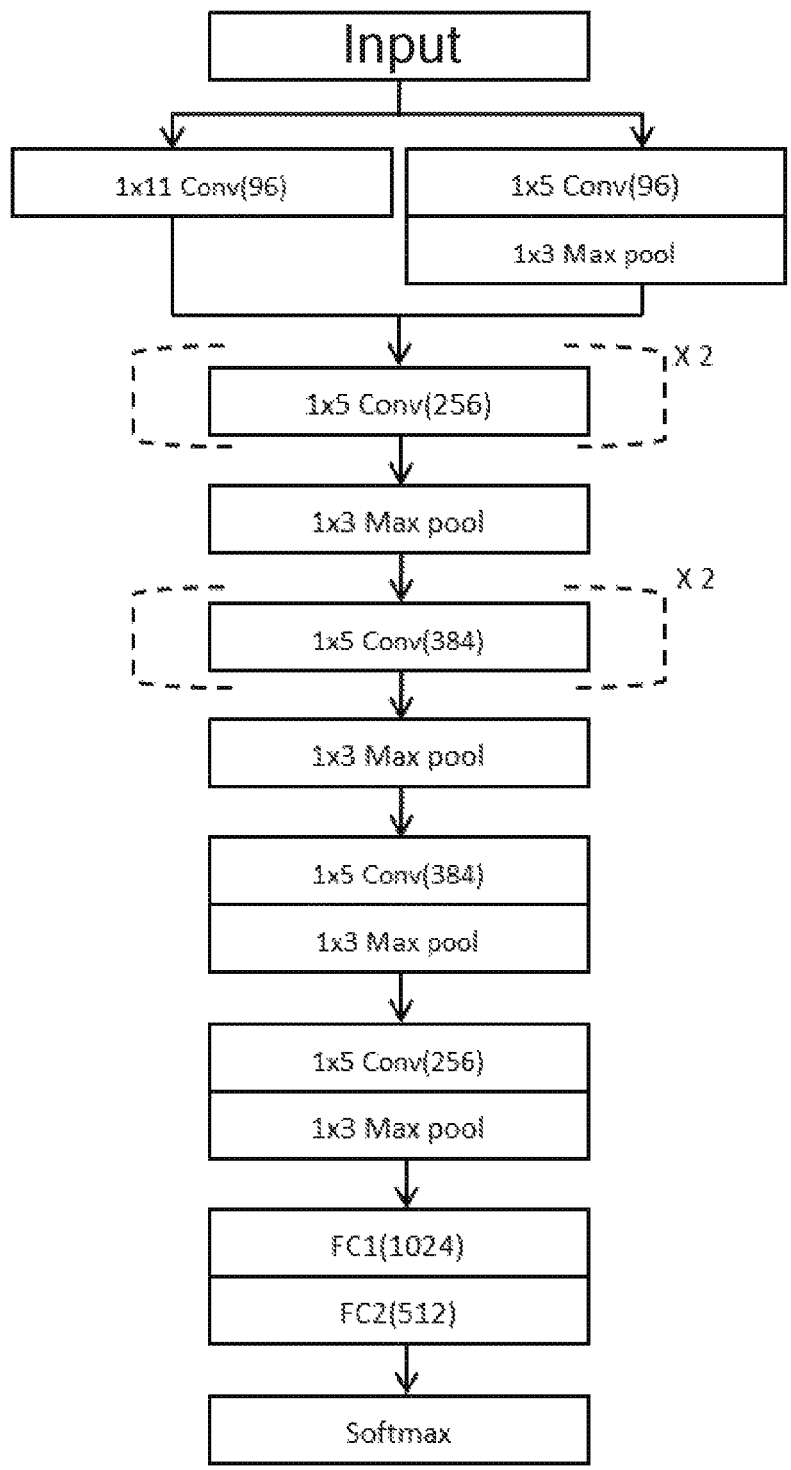
FIG. 4 is a schematic diagram illustrating a heartbeat classification model according to an embodiment of the present disclosure.

The heartbeat classification model adopted in this step may be shown in FIG. 4, which specifically may be an end-to-end multi-label classification model inspired by CNN models based on artificial intelligence deep learning such as AlexNet, VGG16, Inception. Specifically, the network of this model is a seven-layer convolution network, and each convolution is followed by an activation function. A first layer is a convolution layer having two different scales, followed by six convolution layers. The numbers of convolution kernels of the seven-layer convolution are 96, 256, 256, 384, 384, 384 and 256 respectively. Except for the convolution kernel of the first layer, which has two scales of 5 and 11, the convolution kernels of other layers have a scale of 5. Third, fifth, sixth and seventh convolution layers are followed by a pooling layer. Finally, two full connection layers follow.

The heartbeat classification model in this step is obtained by training 17 million data samples of 300,000 patients in a training set. These samples are generated by accurately labeling the data according to requirements of ambulatory electrocardiogram analysis and diagnosis. Labeling is mainly for common arrhythmias, conduction block, ST segment and T wave changes, which may meet model training in different application scenes. Specifically, labeled information is stored in a preset standard data format. In the preprocessing of training data, in order to increase the generalization ability of the model, small sliding is made for a classification with a small sample size to expand the data. Specifically, the data is moved 2 times based on each heartbeat according to a certain step (such as 10-50 data points), so that the data may be increased by 2 times, and the recognition accuracy of classification samples with a small amount of data is improved. The generalization ability has also been verified to be improved from the actual result.

In an actual training process, two GPU servers are used for dozens of round-robin training. After the training converges, 5 million pieces of independent test data are used for testing, and the accuracy rate may reach 91.92%.

An interception length of the training data may be from 1 second to 10 seconds. For example, a sample rate is 200 Hz, a sample length is 2.5 s, an obtained data length is a segment D [500] of 500 electrocardiogram voltage values (millivolts), and input data is: InputData (i, j), wherein i is an i-th lead, and j is a j-th segment of the i-th lead. All input data is randomly scattered before training, which ensures convergence of the training process. At the same time, collection of too many samples from the electrocardiogram data of a same patient is limited, which improves the generalization ability of the model, that is, an accuracy rate in a real scene. During the training, segment data D corresponding to all leads is synchronously input, and lead data of multiple spatial dimensions (different electrocardiogram axis vectors) of each time position is synchronously learned according to a multi-channel analysis method of image analysis, so that a more accurate classification result than a conventional algorithm is obtained.

Step 137, the heartbeat analysis data of particular heartbeats in results of the primary classification information is input into a ST segment and T wave change model for identification, and ST segment and T wave evaluation information is determined.

The ST segment and T wave evaluation information is lead position information that the ST segment and T wave corresponding to the heartbeat analysis data is changed. In clinical diagnosis, changes for the ST segment and T wave are required to be located to a specific lead.

Wherein, the data of the particular heartbeats of the primary classification information refers to the heartbeat analysis data including sinus heartbeat (N) and other heartbeat types that may include ST segment changes.

The data of particular heartbeats in the primary classification information is put into a trained artificial intelligence deep learning model for identifying the ST segment and T wave changes according to each lead in turn by a ST segment and T wave change lead location module, and calculation and analysis is performed. An output result indicates whether features of lead segments conform to the conclusion that ST segment and T wave change, so that the information of leads where the ST segment and T wave changes occur may be determined, that is, the ST segment and T wave evaluation information. The specific method may be as follows: the heartbeat analysis data of each lead that the results in the primary classification information is the sinus heartbeat is put into the ST segment and T wave change model, and the sinus heartbeat data is identified and judged one by one, so as to determine whether the sinus heartbeat has characteristics of ST segment and T wave change and specific lead position information that the change occurs, and the ST segment and T wave evaluation information is determined.

Figure 5:
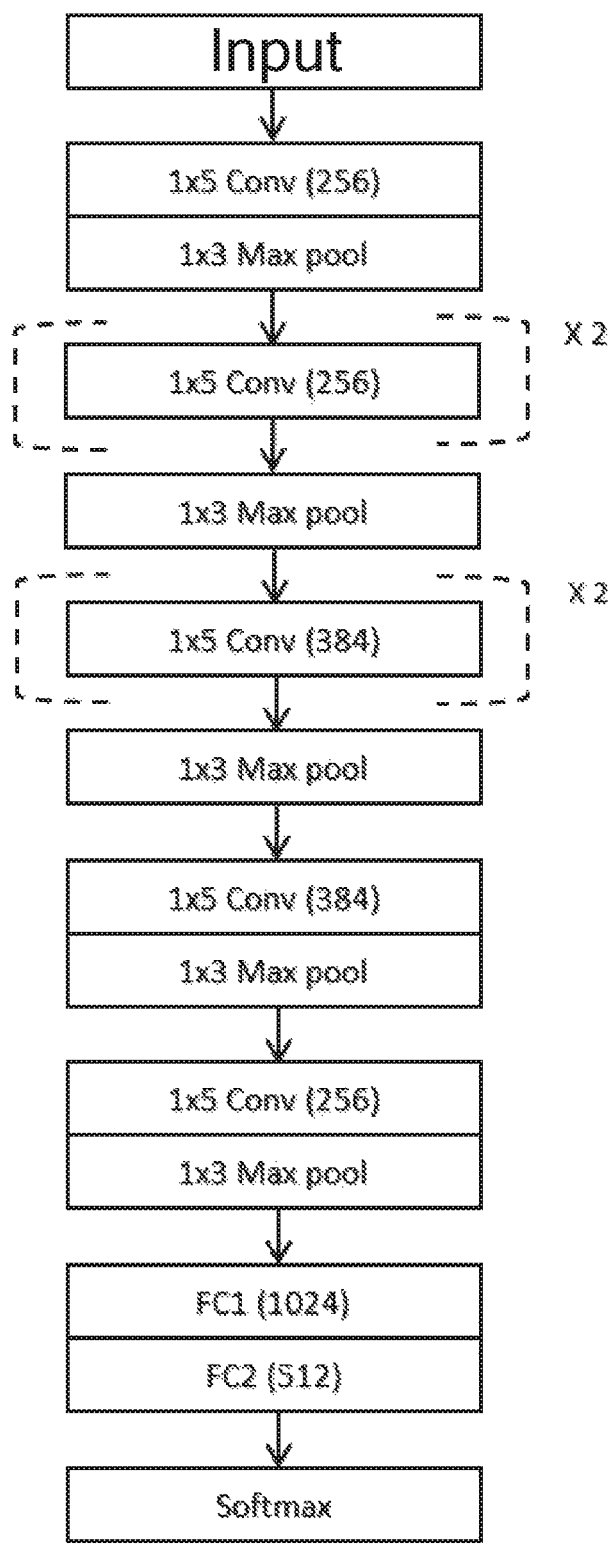
FIG. 5 is a schematic diagram illustrating a ST segment and T wave change model according to an embodiment of the present disclosure.

The ST segment and T wave change model adopted in this step may be as shown in FIG. 5, and it may be an end-to-end classification model inspired by CNN models based on artificial intelligence deep learning such as AlexNet and VGG16. Specifically, the model is a seven-layer network, which includes seven layers of convolution, five layers of pooling and two layers of full connection. A convolution kernel used in all layers of convolution is 1×5, and the number of filters for each layer of the convolution is different. The number of the filters for a first layer of convolution is 96; a second layer of convolution and a third layer of convolution are used together, and the number of the filters is 256; a fourth layer of convolution and a fifth layer of convolution are used together, and the number of the filters is 384; the number of the filters for a sixth layer of convolution is 384; the number of the filters for a seventh layer of convolution is 256. The first, third, fifth, sixth and seventh layers of convolution are followed by the layers of pooling, and then, the two layers of full connection follow. Finally, a Softmax classifier is used to divide the results into two categories. In order to increase the nonlinearity of the model and extract the features of high dimensions of the data, the mode that two layers of convolution are used together is adopted.

Since a proportion of the heartbeat with the ST segment and T wave changes in all heartbeats is relatively low, in order to take into account a diversity of the training data and a balance of the amount of data in each category, a ratio of training data without ST segment and T wave changes and with ST segment and T wave changes is selected about 2:1, which ensures the good generalization ability of the model in the process of classification and avoid to appear a tendency of a category accounting for a relatively large proportion in the training data. Forms of the heartbeat are diverse and different individuals show different forms, therefore, in order to make the model estimate distribution of each classification well and extract features effectively, training samples are collected from individuals of different ages, weights, genders and residential areas. In addition, since the electrocardiogram data of a single individual in a same time period is often highly similar, in order to avoid over-learning, when obtaining the data of the single individual, a small number of samples in different time periods are randomly selected from all the data. Finally, due to characteristics that the forms of the heartbeat of patients have large differences between individuals and high similarity within the individual, different patients are divided into different data sets when dividing training sets and test sets, so as to prevent the data of a same individual from appearing in the training sets and test sets at the same time. Therefore, test results of the obtained model are closest to real application scenes, ensuring the reliability and universality of the model.

Step 138, P wave and T wave feature detection is performed on the heartbeat analysis data according to the heartbeat time sequence data to determine detailed feature information of the P wave and the T wave in each heartbeat.

Specifically, the detailed feature information includes data of amplitudes, directions, forms and starting-ending time. In the analysis of the heartbeat signals, the features of the P wave, T wave and QRS complex are also important basis for the electrocardiogram analysis.

In the P wave and T wave feature detection module, the features of the P wave, T wave, and QRS complex are extracted by calculating a position of a segmentation point of the QRS complex and a position of a segmentation point of the P wave and the T wave, which may be realized by QRS complex segmentation point detection, single-lead PT detection algorithms and multi-lead PT detection algorithms respectively.

The QRS complex segmentation point detection: according to a segment power maximum point and starting and ending points of the QRS complex provided by QRS complex detection algorithms, a R point, R' point, S point and S' point of the QRS complex in a single lead are searched. When there is multi-lead data, a median of each segmentation point is calculated as the final position of the segmentation point.

The single-lead P wave and T wave detection algorithms: compared with the QRS complex, the P wave and T wave are relatively low in amplitude and gentle in signal, and easy to be submerged in the low-frequency noise, which is a difficult in the detection. In this method, according to a result of the QRS complex detection, third filtering is performed on the signals by using a low-pass filter to increase relative amplitudes of the P and T waves after eliminating an influence of the QRS complex on low-frequency bands. The T wave is then searched between two QRS complexes by the peak detection. Since the T wave is a wave complex generated by ventricular repolarization, there is a definite time-locked relationship between the T wave and the QRS complex. Based on the detected QRS complex, a midpoint between each QRS complex and next QRS complex (e.g., limited to a range from 400 ms to 600 ms after a first QRS complex) is taken as an ending point of the T wave detection, and the largest peak in this range is taken as the T wave. Then a peak with the largest amplitude in remaining peaks is selected as the P wave. At the same time, direction and morphology features of the P wave and the T wave are determined according to peak values and position data of the P wave and the T wave. Preferably, a cut-off frequency of the low-pass filtering is set from 10 Hz to 30 Hz.

The multi-lead P wave and T wave detection algorithms: in the case of multiple leads, each wave in a heartbeat is generated at same time, but has different space distribution, while the noise has different time and space distribution, therefore the P and T waves may be detected by tracing algorithms. Firstly, QRS complex elimination processing is performed on the signals and third filtering is performed on the signals by using a low-pass filter to remove interference, and then individual independent components of an original waveform are calculated by an independent component analysis algorithm. In separated individual independent components, corresponding components are selected as P wave and T wave signals according to distribution characteristics of peaks and the position of the QRS complex, and the direction and morphology features of the P wave and the T wave are determined.

Step 139, secondary classification processing is performed on the heartbeat analysis data according to the electrocardiogram basic rule reference data, the detailed feature information of the P wave and T wave and the ST segment and T wave evaluation information under the primary classification information to obtain heartbeat classification information; the heartbeat classification information is analyzed and matched to generate the electrocardiogram event data.

The electrocardiogram basic rule reference data, such as a minimum time interval between two heartbeats, and a minimum interval between the P wave and R wave, is generated according to the description of basic rules of cardiomyocytes electrophysiological activities and electrocardiogram clinical diagnosis in authoritative electrocardiogram textbooks, and which is used for subdividing the primary classification information after classification of the heartbeat mainly based on the RR interval between the heartbeats and a medical significance of different heartbeat signals on each lead. According to the electrocardiogram basic rule reference data combined with classification and identification of a certain number of continuous heartbeats and the detailed feature information of the P wave and T wave, a class of ventricular heartbeats is divided into more detailed heartbeat classes by the heartbeat verification module, including ventricular premature beat (V), ventricular escape beat (VE), ventricular tachycardia beat (VT), and supraventricular heartbeats are subdivided into supraventricular premature beat (S), atrial escape beat (SE), junctional escape beat (JE) and atrial tachycardia premature beat (AT), etc.

In addition, through the secondary classification processing, erroneous classification identification that does not conform to the electrocardiogram basic rule reference data in the primary classification may also be corrected. The subdivided heartbeat classifications are pattern matched according to the electrocardiogram basic rule reference data, classification identification which does not conform to the electrocardiogram basic rule reference data is found, and corrected to a reasonable classification according to the RR interval and classification labels before and after.

Specifically, after the secondary classification processing, a variety of heartbeat classifications may be output, such as: normal sinus heartbeat (N), complete right bundle branch block (N_CRB), complete left bundle branch block (N_CLB), intraventricular block (N_VB), first degree atrioventricular block (N_B1), pre-excitation (N_PS), ventricular premature beat (V), ventricular escape beat (VE), ventricular tachycardia beat (VT), supraventricular premature beat (S), atrial escape beat (SE), junctional escape beat (JE), atrial tachycardia beat (AT), atrial flutter/atrial fibrillation (AF) and artifact (A).

The calculation of basic heart rate parameters may also be completed through this step. The calculated basic heart rate parameters include the RR interval, heart rate, QT time, QTc time and other parameters.

Then, according to results of the secondary classification of the heartbeats, pattern matching is performed according to the electrocardiogram basic rule reference data, and the following typical electrocardiogram events corresponding to the electrocardiogram event data may be obtained, including but not limited to:

supraventricular premature beat
pairs of supraventricular premature beat
supraventricular premature beat bigemini
supraventricular premature beat trigemini
atrial escape beat
atrial escape rhythm
junctional escape beat
junctional escape rhythm
non-paroxysmal supraventricular tachycardia
fastest supraventricular tachycardia
longest supraventricular tachycardia
supraventricular tachycardia
short supraventricular tachycardia
atrial flutter-atrial fibrillation
ventricular premature beat
pairs of ventricular premature beat
ventricular premature beat bigeminy
ventricular premature beat trigemini
ventricular escape beat
ventricular escape rhythm
accelerated idioventricular rhythm
fastest ventricular tachycardia
longest ventricular tachycardia
ventricular tachycardia
short ventricular tachycardia
second-degree type I sinoatrial block
second-degree type II sinoatrial block
first-degree atrioventricular block
second-degree type I atrioventricular block
second-degree type II atrioventricular block
second-degree type II (2:1) atrioventricular block
high-degree atrioventricular block
complete left bundle branch block
complete right bundle branch block
intraventricular block
pre-excitation syndrome
ST segment and T wave change
longest RR interval The electrocardiogram event data is generated from the heartbeat analysis data according to the heartbeat classification information and the electrocardiogram basic rule reference data. The electrocardiogram event data includes device ID information of the ambulatory monitoring device.

Step 140, the ambulatory monitoring device determines corresponding electrocardiogram event information according to the electrocardiogram event data, and determines whether the electrocardiogram event information is the electrocardiogram abnormal event information.

Specifically, after the electrocardiogram event data is obtained, corresponding electrocardiogram event information may be obtained correspondingly through a corresponding relationship between the electrocardiogram event data and the time information of the electrocardiogram which is obtained through artificial intelligence learning, for example, the electrocardiogram event information corresponding to the electrocardiogram event data is sinus heartbeat event, ventricular premature beat event, etc., only some of which are electrocardiogram abnormal events that need to be generated alarms.

The above data processing is all real-time, so the ambulatory monitoring device continuously generates the electrocardiogram event information. In practical application, the output interval of the electrocardiogram event information may also be reasonably set, not only reducing the amount of data calculation, but also avoiding the missed detection.

The electrocardiogram event information is matched with the electrocardiogram abnormal event information recorded in the ambulatory monitoring device after being obtained. If the electrocardiogram event information is electrocardiogram abnormal event information, step 150 is executed, otherwise step 120 is continued, and collecting the monitoring data for the tested object is continued.

Step 150, the alarm information is output.

Specifically, when the electrocardiogram event information is determined to be the electrocardiogram abnormal event information, corresponding alarm information is generated by the ambulatory monitoring device according to the electrocardiogram abnormal event information.

The alarm information may be output locally in the ambulatory monitoring device, which may be simply a preset sound alarm, photoelectric alarm, or a voice alarm, information display alarm and the like output according to time information of electrocardiogram abnormalities.

Abnormal is prompted for the current electrocardiogram signals of the monitored object by generating the alarm, so that the monitored object may be alerted quickly.

In order to effectively record the abnormalities, preferably, when the electrocardiogram event information is determined to be the electrocardiogram abnormal event information, the ambulatory monitoring device generates abnormal event recording data according to the electrocardiogram data, electrocardiogram event data, alarm information of the electrocardiogram event information, as well as a plurality of pieces of electrocardiogram data within a preset time period before and after acquisition time (i.e., a time corresponding to alarm time information) for obtaining the electrocardiogram data for which the alarm information is generated.

The abnormal event recording data is stored in the ambulatory monitoring device for retrospective use in electrocardiogram abnormality analysis.

The present disclosure not only may realize local alarm output and remind the user of the occurrence of the electrocardiogram abnormal event, but also may report the electrocardiogram abnormal event through data interaction with the server. Remote monitoring may also be realized by reporting, so that monitoring staff logging in the server may correspondingly response, such as assign medical rescuer, remotely guiding users to do emergency treatment, or guiding medical treatment, etc.

Figure 6:
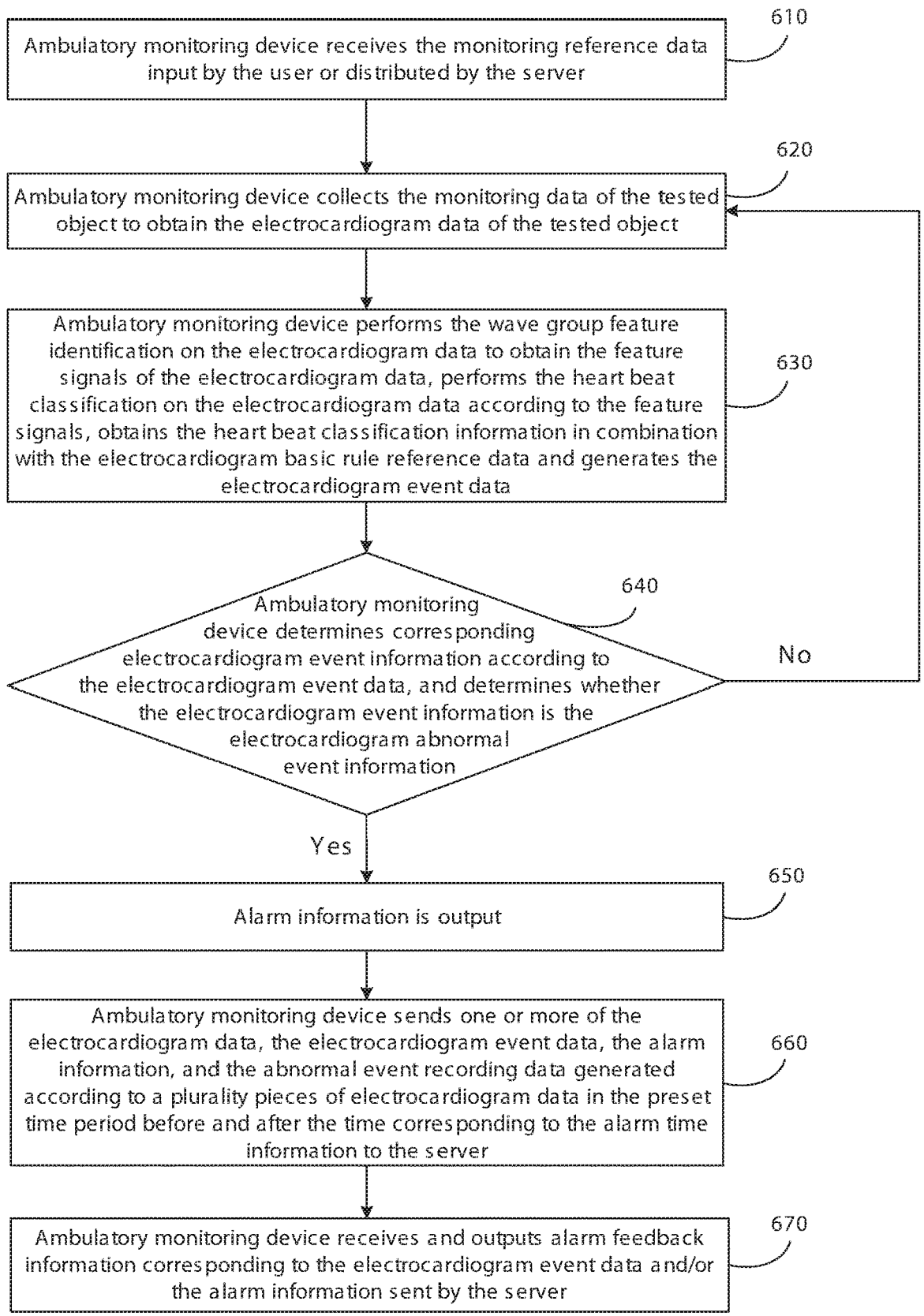
FIG. 6 is a flowchart illustrating another electrocardiogram information ambulatory monitoring method according to an embodiment of the present disclosure.

In order to achieve the above purpose, the electrocardiogram information ambulatory monitoring method of the present disclosure may be shown in FIG. 6, and includes the following steps:

Step 610, the ambulatory monitoring device receives the monitoring reference data input by the user or distributed by the server.

Step 620, the ambulatory monitoring device collects the monitoring data of the tested object to obtain the electrocardiogram data of the tested object.

Step 630, the ambulatory monitoring device performs the waveform feature identification on the electrocardiogram data to obtain the feature signals of the electrocardiogram data, performs the heartbeat classification on the electrocardiogram data according to the feature signals, obtains the heartbeat classification information with the electrocardiogram basic rule reference data and generates the electrocardiogram event data.

Step 640, the ambulatory monitoring device determines corresponding electrocardiogram event information according to the electrocardiogram event data, and determines whether the electrocardiogram event information is the electrocardiogram abnormal event information.

If the electrocardiogram event information is the electrocardiogram abnormal event information, step 650 is executed, otherwise step 620 is continued, and collecting the monitoring data for the tested object is continued.

Step 650, the alarm information is output.

The above steps are the same as steps 110-150 of the previous embodiment, and will not be described here.

Step 660, the ambulatory monitoring device sends one or more of the electrocardiogram data, the electrocardiogram event data, the alarm information, and the abnormal event recording data generated according to a plurality of pieces of electrocardiogram data in the preset time period before and after the time corresponding to the alarm time information to the server.

Specifically, the ambulatory monitoring device may be connected to the server for data transmission through a wired mode or a wireless network. Preferably, the wireless network is used to realize data transmission during real-time data transmission.

The wireless network includes wireless but not limited to wireless local area network based on IEEE 802.11b standard (WIFI), Bluetooth, 3G/4G/5G mobile communication network, internet of things and other means.

After outputting the alarm information or while outputting the alarm information, the ambulatory monitoring device may send one or more of the electrocardiogram data, the electrocardiogram event data, the alarm information, and the abnormal event recording data generated according to a plurality of pieces of electrocardiogram data in the preset time period before and after the time corresponding to the alarm time information to the server through the wired mode or the wireless network.

The server may realize remote monitoring according to the received information, and may further process the above information through the server, such as sending the information to terminal devices of relevant medical institutions, determining subsequent processing programs according to the above information, sending rescuer, remotely guiding users to do emergency treatment, or guiding medical treatment, etc.

In a preferred solution, the ambulatory monitoring device may be located through the network, and current position information of the monitored object may be reported in the sent alarm information, so that the server may acquire the real-time position information of the monitored object.

Step 670, the ambulatory monitoring device receives and outputs alarm feedback information corresponding to the electrocardiogram event data and/or the alarm information sent by the server.

In a preferred solution, when generating subsequent processing for the received information, the server may also feed back to the ambulatory monitoring device. For example, when sending the rescue personnel to the monitored user according to the alarm information, the server generates notification information sent to the ambulatory monitoring device for output, and informs the monitored object that the rescue personnel have been sent; or when generating emergency processing information according to the alarm information, the server sends the emergency processing information to the ambulatory monitoring device and outputs, and guides the monitored object to take corresponding actions, such as sitting in situ, lying flat, taking medicine immediately or seeking medical treatment quickly, etc. Output modes include but are not limited to voice playback or display output.

In addition, the ambulatory monitoring device may also support the user to actively trigger event recording. When the user is aware of physically unwell, he may use the ambulatory monitoring device to input his own symptoms by voice, text and other means. The ambulatory monitoring device generates an active alarm event record according to the information input by the user and sends it to the server.

Figure 7:
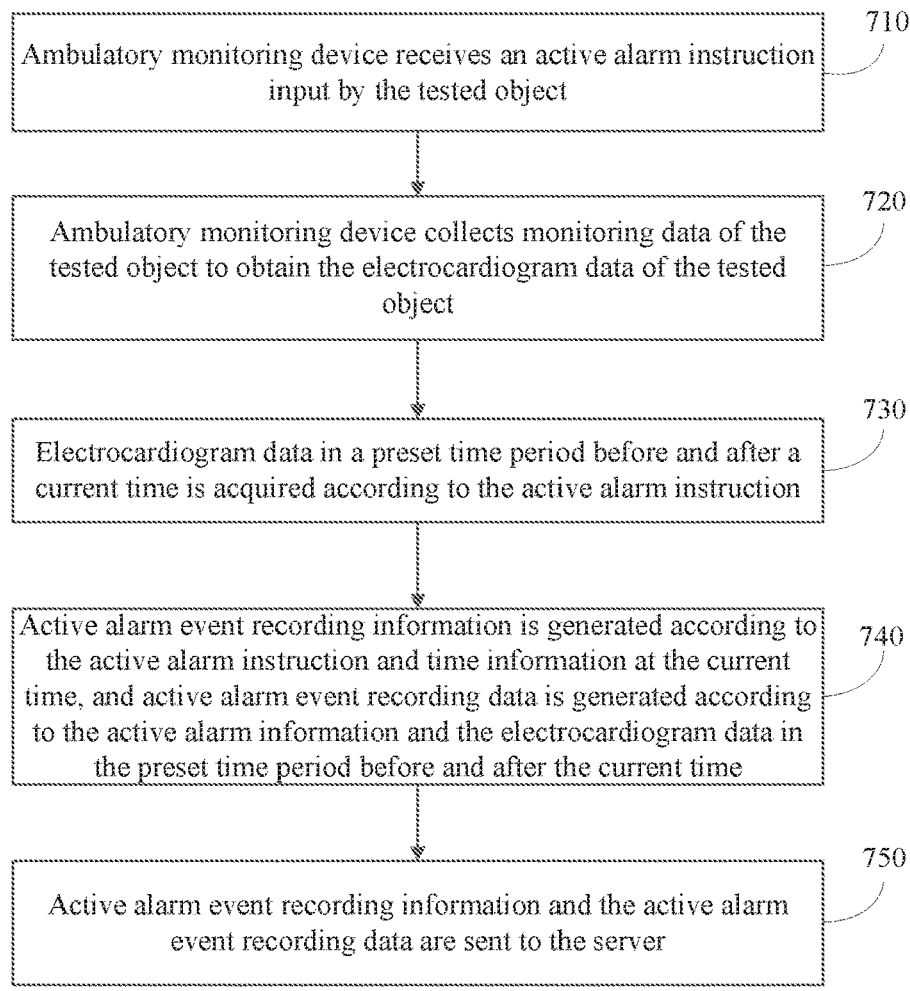
FIG. 7 is a flowchart illustrating a method for actively triggering event record by a user according to an embodiment of the present disclosure.

The specific implementation process may be shown in FIG. 7, including the following steps:

Step 710, the ambulatory monitoring device receives an active alarm instruction input by the tested object.

Specifically, for the convenience of users, the trigger of the active alarm instruction may be designed on the ambulatory monitoring device through hardware keys, adopting a one-button trigger mode, or may be a functional option on a human-computer interaction interface of the ambulatory monitoring device, and the input of the active alarm instruction may be realized through user operation.

Step 720, active alarm information input by the tested object is received according to the active alarm instruction.

Specifically, when receiving the active alarm instruction, the ambulatory monitoring device generates an input device starting instruction to start the input device on the ambulatory monitoring device, which may be a voice input device, a video and audio input device, a text information input device, etc. Specifically, the input device may be a microphone, a camera, a soft keyboard, a touch screen or the like.

After the input device is started, the input of the user is monitored, and the monitored information is recorded as the active alarm information.

Step 730, the electrocardiogram data in a preset time period before and after a current time is acquired according to the active alarm instruction.

When receiving the active alarm instruction, the ambulatory monitoring device further records the electrocardiogram data in the preset time period before and after the time when the active alarm instruction is generated for analysis to confirm the reason why the user feels uncomfortable.

Step 730 and step 720 may be performed simultaneously.

Step 740, active alarm event recording information is generated according to the active alarm instruction and time information at the current time, and active alarm event recording data is generated according to the active alarm information and the electrocardiogram data in the preset time period before and after the current time.

When the active alarm instruction is generated, the ambulatory monitoring device records the current time and generates the active alarm event recording information to indicate the event that the user actively alarms is generated. In addition, the active alarm event recording data is generated based on the active alarm information recorded in step 720 and the electrocardiogram data recorded in step 730. The active alarm event recording information and the active alarm event recording data are related, and the active alarm event recording data may be obtained through the active alarm event recording information.

Step 750, the active alarm event recording information and the active alarm event recording data are sent to the server.

Specifically, the ambulatory monitoring device automatically uploads the active alarm event recording information and the active alarm event recording data to the server after the recording is completed. Before uploading, the ambulatory monitoring device firstly determines the communication connection state with the server. If it is in a normal connection state, the data may be uploaded directly or stored locally synchronously. If it is in a disconnection state, the active alarm event recording information and the active alarm event recording data may be cached in the local memory of the ambulatory monitoring device, a communication connection request with the server is initiated according to a preset time interval, and the active alarm event recording information and the active alarm event recording data are uploaded automatically after the connection is completed.

Figure 8:
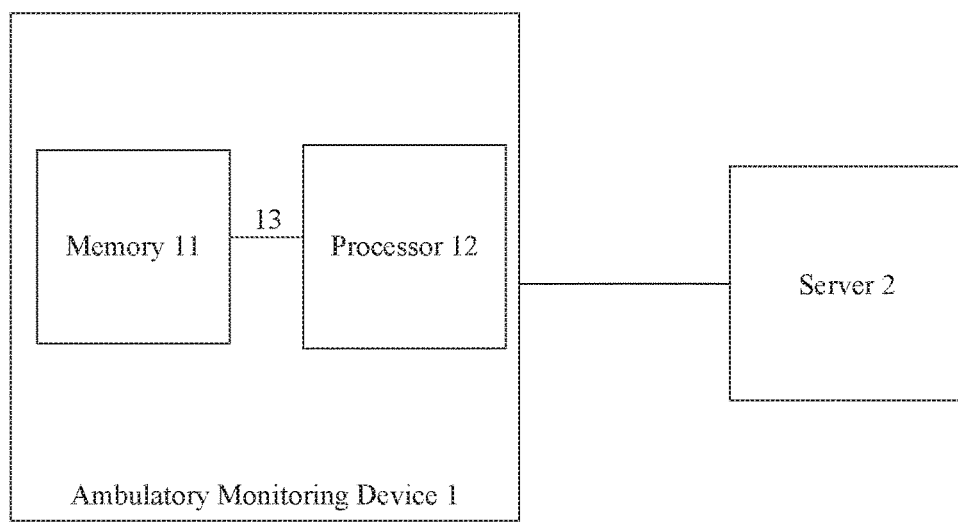
FIG. 8 is a schematic structural diagram illustrating an ambulatory monitoring system according to an embodiment of the present disclosure.

Correspondingly, FIG. 8 is a schematic structural diagram of an ambulatory monitoring system provided by an embodiment of the present disclosure. The ambulatory monitoring system includes one or more ambulatory monitoring devices 1 and a server 2. The ambulatory monitoring device 1 includes a processor 12 and a memory 11. The memory 11 may be connected to the processor 12 via a bus 13. The memory 11 may be a non-volatile memory such as hard disk drive and flash memory, and the memory 11 stores software programs and device drivers. The software programs may perform various functions of the above methods provided by the embodiments of the present disclosure; the device drivers may be network and interface drivers. The processor 12 is used for executing the software programs, and when the software programs are executed, the methods provided by the embodiments of the present disclosure may be realized.

It should be noted that an embodiment of the present disclosure also provides a computer readable storage medium. The computer readable storage medium stores computer programs, and when the computer programs are executed by the processor, the method provided by the embodiments of the present disclosure may be realized.

An embodiment of the present disclosure also provides a computer program product including instructions. When the computer program product runs on a computer, the processor performs the above method.

The electrocardiogram information ambulatory monitoring method and the ambulatory monitoring system according to the embodiments of the present disclosure perform complete and rapid automatic analysis of the electrocardiogram data through the ambulatory monitoring device, detect abnormalities in time and generate the alarm information, and simultaneously support the users to actively report alarms when they are aware of abnormalities. The data is recorded and stored for the cases in which abnormal alarms are generated, so that the reason that causes abnormalities may be quickly analyzed and it can be traced.

In the above embodiment, the electrocardiogram information ambulatory monitoring method is mainly implemented in the ambulatory monitoring device. In fact, the electrocardiogram information ambulatory monitoring method of the present disclosure may also be implemented in the server. The ambulatory monitoring device mainly performs the collection and transmission of the electrocardiogram data, the output of the alarm information and the triggering of the active alarm. In the following, a brief description will be given with an embodiment, and each specific processing procedure and repeated parts in the above embodiments will not be described again.

Figure 9:
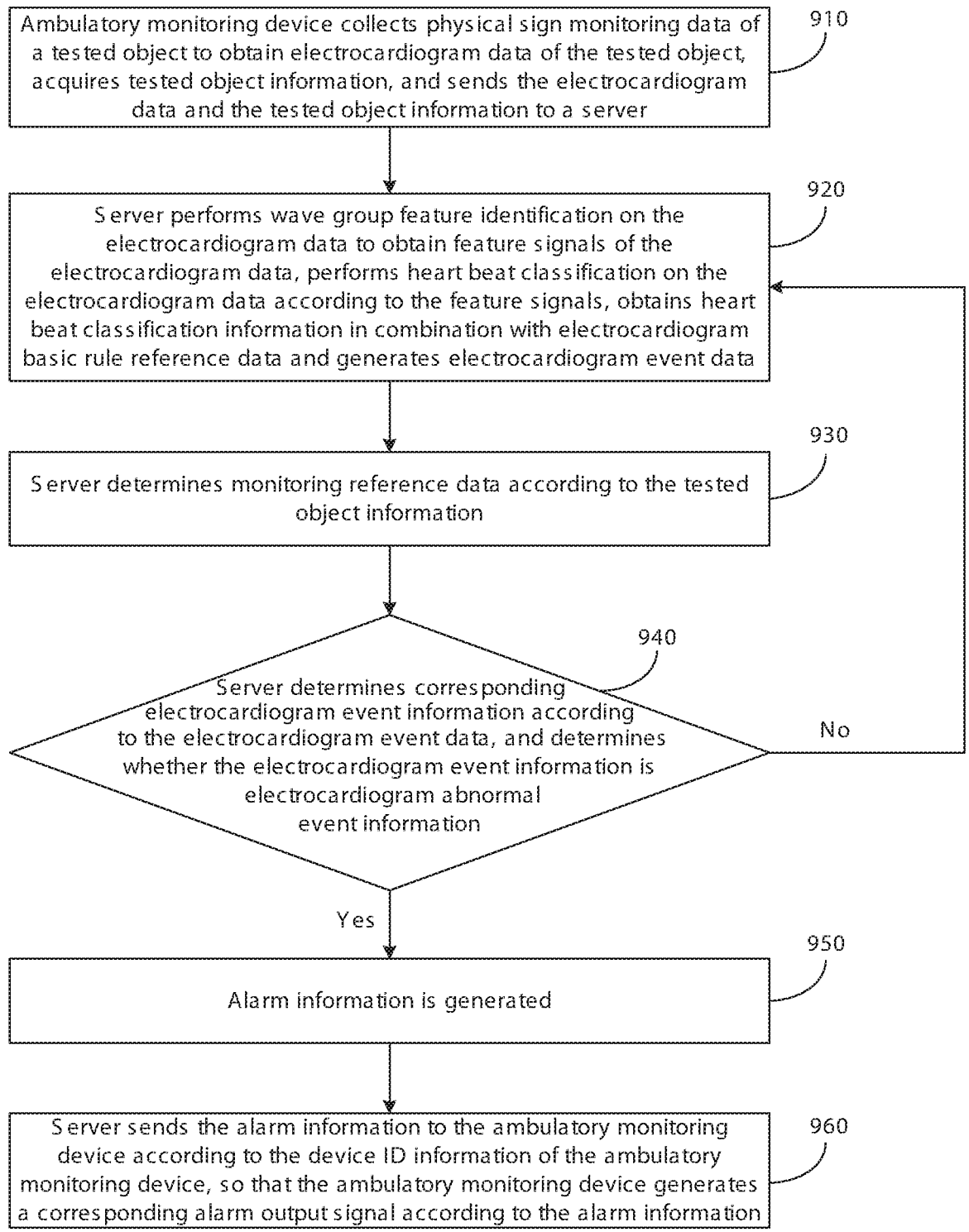
FIG. 9 is a flowchart illustrating another electrocardiogram information ambulatory monitoring method according to an embodiment of the present disclosure.

The electrocardiogram information ambulatory monitoring method of the present disclosure will be described in detail with reference to the flowchart of the electrocardiogram information ambulatory monitoring method shown in FIG. 9. In this embodiment, the electrocardiogram information ambulatory monitoring method is mainly implemented in the server. As shown in FIG. 9, the electrocardiogram information ambulatory monitoring method of the present disclosure mainly includes the following steps:

Step 910, an ambulatory monitoring device collects physical sign monitoring data of a tested object to obtain electrocardiogram data of the tested object, obtains tested object information, and sends the electrocardiogram data and the tested object information to a server.

The electrocardiogram data has time attribute information and device ID information of the ambulatory monitoring device.

Step 920, the server performs waveform feature identification on the electrocardiogram data to obtain feature signals of the electrocardiogram data, performs heartbeat classification on the electrocardiogram data according to the feature signals, obtains heartbeat classification information with electrocardiogram basic rule reference data and generates electrocardiogram event data.

The specific execution process of this step is the same as that of the previous step 120, except that the execution subject becomes the server.

Step 930, the server determines monitoring reference data according to the tested object information.

The server determines appropriate monitoring reference data according to the tested object information sent by the ambulatory monitoring device, which may be specifically determined by combining the age, gender, medical history and the like in the tested object information, and preferably, historical monitoring data may also be obtained according to the tested object information, and personalized monitoring reference data facing the tested object is determined by combining the historical monitoring data. The monitoring reference data should include at least electrocardiogram abnormal event information corresponding to the tested object information.

Step 940, the server determines corresponding electrocardiogram event information according to the electrocardiogram event data, and determines whether the electrocardiogram event information is electrocardiogram abnormal event information.

The specific execution process of this step is the same as that of the previous step 140, except that the implementor is different.

When the electrocardiogram event information is the electrocardiogram abnormal event information, step 950 is executed, otherwise step 910 is continued.

Step 950, alarm information is generated.

Specifically, when the server determines that the electrocardiogram event information is the electrocardiogram abnormal event information, corresponding alarm information is generated according to the electrocardiogram abnormal event information.

The alarm information includes the electrocardiogram abnormal event information, alarm time information and the device ID information of the ambulatory monitoring device.

At the same time, when the electrocardiogram event information is determined to be the electrocardiogram abnormal event information, through the server, abnormal event recording data is generated from the electrocardiogram data, electrocardiogram event data, alarm information of the electrocardiogram event information, as well as a plurality of pieces of electrocardiogram data within a preset time period before and after acquisition time (i.e., a time corresponding to the alarm time information) for obtaining the electrocardiogram data for which the alarm information is generated. The abnormal event recording data is stored in the server for retrospective use in electrocardiogram abnormality analysis.

Step 960, the server sends the alarm information to the ambulatory monitoring device according to the device ID information of the ambulatory monitoring device, so that the ambulatory monitoring device generates a corresponding alarm output signal according to the alarm information.

Specifically, the server determines the ambulatory monitoring device according to the device ID and sends the alarm information to the ambulatory monitoring device through the communication connection with the ambulatory monitoring device.

The ambulatory monitoring device generates the alarm output signal according to the received alarm information. Specifically, the alarm output signal may be simply a predetermined sound alarm, photoelectric alarm, or a voice alarm, information display alarm and the like output according to time information of electrocardiogram abnormalities. Abnormal is prompted for the current electrocardiogram signals of the monitored object by generating the alarm, so that the monitored object may be alerted quickly.

Similarly, the server may perform remote monitoring as described in the above embodiment, so that monitoring staff logging in the server may make corresponding responses, such as sending medical rescuer or remotely guiding users to do emergency treatment, guiding medical treatment, etc. Specifically, positioning may be carried out through the network to determine current position information of the ambulatory monitoring device, so that the server may obtain the real-time position information of the monitored object.

Similarly, the server may also send feedback information to the ambulatory monitoring device. For example, when sending the rescue personnel to the monitored user according to the alarm information, the server generates notification information and sends it to the ambulatory monitoring device for output, and informs the monitored object that the rescue personnel have been sent; or when generating emergency processing information according to the alarm information, the server sends the emergency processing information to the ambulatory monitoring device and outputs, and guides the monitored object to take corresponding actions, such as sitting in situ, lying flat, taking medicine immediately or seeking medical treatment quickly, etc. Output modes include but are not limited to voice playback or display output.

Users actively trigger event recording may also be realized in this embodiment, the processing procedure is the same as that of the previous embodiment, and will not be repeated here.

Figure 10:
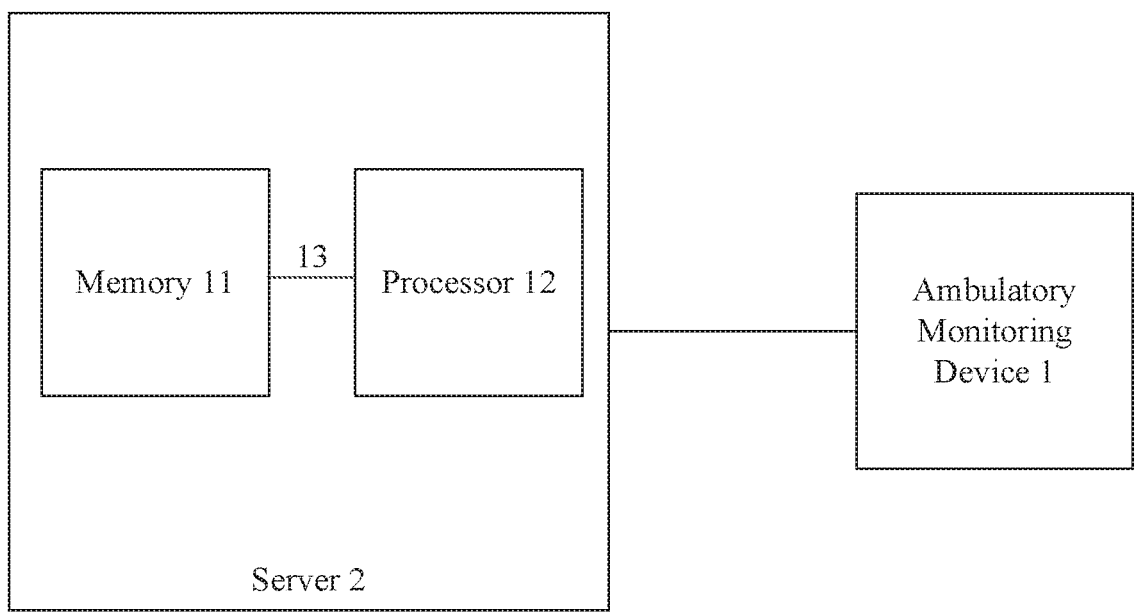
FIG. 10 is a schematic structural diagram illustrating another ambulatory monitoring system according to an embodiment of the present disclosure.

Correspondingly, FIG. 10 is a schematic structural diagram of an ambulatory monitoring system provided by an embodiment of the present disclosure. The ambulatory monitoring system includes one or more ambulatory monitoring devices 1 and a server 2. The server 2 includes a processor 12 and a memory 11. The memory 11 may be connected to the processor 12 via a bus 13. The memory 11 may be a non-volatile memory such as hard disk drive and flash memory, and the memory 11 stores software programs and device drivers. The software programs may perform various functions of the above methods provided by the embodiments of the present disclosure; the device drivers may be network and interface drivers. The processor 12 is used for executing the software programs, and when the software programs are executed, the methods provided by the embodiments of the present disclosure may be realized.

It should be noted that an embodiment of the present disclosure also provides a computer readable storage medium. The computer readable storage medium stores computer programs, and when the computer programs are executed by the processor, the method provided by the embodiments of the present disclosure may be realized.

An embodiment of the present disclosure also provides a computer program product including instructions. When the computer program product runs on a computer, the processor performs the above method.

The electrocardiogram information ambulatory monitoring method and the ambulatory monitoring system according to the embodiments of the present disclosure collect the electrocardiogram data through the ambulatory monitoring device, upload the electrocardiogram data to the server for complete and rapid automatic analysis, timely discover abnormalities, generate the alarm information and send to the ambulatory monitoring device, and meanwhile, the ambulatory monitoring device supports users to actively report the alarm they are aware of abnormalities. The server records and stores the data for the cases in which abnormal alarms are generated, so that causes of abnormalities may be quickly analyzed and have traceability.

Those skilled in the art should further realize that the units and algorithm steps of the examples described in the embodiments disclosed herein may be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc., made within the spirit and principles of the present disclosure should be included in the scope of protection of the present disclosure.

What is claimed is:

1. An electrocardiogram information ambulatory monitoring method, comprising:
    receiving, by an ambulatory monitoring device, monitoring reference data input by a user or distributed by a server; wherein the monitoring reference data comprises patient information and electrocardiogram abnormal event information;
    collecting, by the ambulatory monitoring device, monitoring data of the patient to obtain electrocardiogram data of the patient;
    performing, by the ambulatory monitoring device, waveform feature identification on the electrocardiogram data to obtain feature signals of the electrocardiogram data, performing heartbeat classification on the electrocardiogram data according to the feature signals, obtaining heartbeat classification information with electrocardiogram basic rule reference data and generating electrocardiogram event data; wherein the electrocardiogram event data comprises device ID information of the ambulatory monitoring device; and
    determining, by the ambulatory monitoring device, corresponding electrocardiogram event information according to the electrocardiogram event data, and determining whether the electrocardiogram event information is the electrocardiogram abnormal event information; and outputting alarm information when the electrocardiogram event information is the electrocardiogram abnormal event information;
    the performing waveform feature identification on the electrocardiogram data to obtain feature signals of the electrocardiogram data, performing heartbeat classification on the electrocardiogram data according to the feature signals, obtaining heartbeat classification information with electrocardiogram basic rule reference data and generating electrocardiogram event data, comprises:
        converting a data format of the electrocardiogram data into a preset standard data format by resampling, and performing a first filtering processing on converted electrocardiogram data in the preset standard data format;
        performing heartbeat detection processing on electrocardiogram data processed by the first filtering processing to identify a plurality of pieces of heartbeat data comprised in the electrocardiogram data, each of which corresponds to a heartbeat cycle, comprising amplitude and starting-ending time data of corresponding P wave, QRS complex and T wave;
        determining a detection confidence level of each heartbeat according to the heartbeat data;
        performing interference identification on the heartbeat data according to a two-class interference identification model to obtain whether there is interference noise in the heartbeat data with a probability value for judging the interference noise;
        determining a validity of the heartbeat data according to the detection confidence level, and, according to lead parameters and the heartbeat data of determined valid heartbeat data, combining and generating heartbeat time sequence data based on results of the interference identification and time rules; and generating heartbeat analysis data according to the heartbeat time sequence data;
        performing feature extraction and analysis of an amplitude and time characterization data on the heartbeat analysis data according to a heartbeat classification model, to obtain primary classification information of the heartbeat analysis data;
        inputting the heartbeat analysis data of particular heartbeats in results of the primary classification information into a ST segment and T wave change model for identification, and determining ST segment and T wave evaluation information;
        performing P wave and T wave feature detection on the heartbeat analysis data according to the heartbeat time sequence data to determine detailed feature information of the P wave and the T wave in each heartbeat, wherein the detailed feature information comprises data of amplitudes, directions, forms and starting-ending time;

performing secondary classification processing on the heartbeat analysis data according to the electrocardiogram basic rule reference data, the detailed feature information of the P wave and the T wave and the ST segment and T wave evaluation information under the primary classification information to obtain heartbeat classification information; and analyzing and matching the heartbeat classification information to generate the electrocardiogram event data.

2. The method according to claim 1, further comprising:
receiving, by the ambulatory monitoring device, an active alarm instruction input by the patient;
receiving active alarm information input by the patient according to the active alarm instruction;
obtaining electrocardiogram data in a preset time period before and after a current time according to the active alarm instruction;
generating active alarm event recording information according to the active alarm instruction and time information at the current time, and generating active alarm event recording data according to the active alarm information and the electrocardiogram data in the preset time period before and after the current time; and
sending the active alarm event recording information and the active alarm event recording data to the server.

3. The method according to claim 1, wherein the alarm information comprises the electrocardiogram abnormal event information, alarm time information and the device ID information of the ambulatory monitoring device, and the method further comprises:
sending, by the ambulatory monitoring device, one or more of the electrocardiogram data, the electrocardiogram event data, alarm information, and abnormal event recording data generated according to a plurality of pieces of electrocardiogram data in a preset time period before and after a time corresponding to the alarm time information to the server.

4. The method according to claim 3, further comprising:
receiving and outputting, by the ambulatory monitoring device, alarm feedback information corresponding to the electrocardiogram event data and/or the alarm information sent by the server.

5. An electrocardiogram information ambulatory monitoring method, comprising:
collecting, by an ambulatory monitoring device, physical sign monitoring data of a patient to obtain electrocardiogram data of the patient, obtaining patient information, and sending the electrocardiogram data and the patient information to a server; wherein the electrocardiogram data has time attribute information and device ID information of the ambulatory monitoring device;
performing, by the server, waveform feature identification on the electrocardiogram data to obtain feature signals of the electrocardiogram data, performing heartbeat classification on the electrocardiogram data according to the feature signals, obtaining heartbeat classification information with electrocardiogram basic rule reference data and generating electrocardiogram event data; wherein the electrocardiogram event data comprises the device ID information of the ambulatory monitoring device;
determining, by the server, monitoring reference data according to the patient information;

wherein the monitoring reference data comprises electrocardiogram abnormal event information corresponding to the patient information;
determining, by the server, corresponding electrocardiogram event information according to the electrocardiogram event data, and determining whether the electrocardiogram event information is electrocardiogram abnormal event information; and generating alarm information if the electrocardiogram event information is electrocardiogram abnormal event information; wherein the alarm information comprises the electrocardiogram abnormal event information, alarm time information and the device ID information of the ambulatory monitoring device; and
sending, by the server, the alarm information to the ambulatory monitoring device according to the device ID information of the ambulatory monitoring device, so that the ambulatory monitoring device generates a corresponding alarm output signal according to the alarm information;
wherein the performing waveform feature identification on the electrocardiogram data to obtain feature signals of the electrocardiogram data, performing heartbeat classification on the electrocardiogram data according to the feature signals, obtaining heartbeat classification information with electrocardiogram basic rule reference data and generating electrocardiogram event data, comprises:
converting a data format of the electrocardiogram data into a preset standard data format by resampling, and performing a first filtering processing on converted electrocardiogram data in the preset standard data format;
performing heartbeat detection processing on electrocardiogram data processed by the first filtering processing to identify a plurality of pieces of heartbeat data comprised in the electrocardiogram data, each of which corresponds to a heartbeat cycle, comprising amplitude and starting-ending time data of corresponding P wave, QRS complex and T wave;
determining a detection confidence level of each heartbeat according to the heartbeat data;
performing interference identification on the heartbeat data according to a two-class interference identification model to obtain whether there is interference noise in the heartbeat data with a probability value for judging the interference noise;
determining a validity of the heartbeat data according to the detection confidence level, and, according to lead parameters and the heartbeat data of determined valid heartbeat data, combining and generating heartbeat time sequence data based on results of the interference identification and time rules; and generating heartbeat analysis data according to the heartbeat time sequence data;
performing feature extraction and analysis of an amplitude and time characterization data on the heartbeat analysis data according to a heartbeat classification model, to obtain primary classification information of the heartbeat analysis data;
inputting the heartbeat analysis data of particular heartbeats in results of the primary classification information into a ST segment and T wave change model for identification, and determining ST segment and T wave evaluation information;
performing P wave and T wave feature detection on the heartbeat analysis data according to the heartbeat time sequence data to determine detailed feature information of the P wave and the T wave in each heartbeat, wherein the detailed feature information comprises data of amplitudes, directions, forms and starting-ending time;

performing secondary classification processing on the heartbeat analysis data according to the electrocardiogram basic rule reference data, the detailed feature information of the P wave and the T wave and the ST segment and T wave evaluation information under the primary classification information to obtain heartbeat classification information; and analyzing and matching the heartbeat classification information to generate the electrocardiogram event data.

6. The method according to claim 5, further comprising:
receiving, by the ambulatory monitoring device, an active alarm instruction input by the patient;
receiving active alarm information input by the patient according to the active alarm instruction;
obtaining electrocardiogram data in a preset time period before and after a current time according to the active alarm instruction;
generating active alarm event recording information according to the active alarm instruction and time information at the current time, and generating active alarm event recording data according to the active alarm information and the electrocardiogram data in the preset time period before and after the current time; and
sending the active alarm event recording information and the active alarm event recording data to the server.

7. The method according to claim 5, further comprising:
if the electrocardiogram event information is electrocardiogram abnormal event information, obtaining, by the server, a plurality of pieces of electrocardiogram data in a preset time period before and after a time corresponding to the electrocardiogram data according to the time attribute information, and generating abnormal event recording data; and
generating, by the server, relationship information between the abnormal event recording data and the alarm information.

8. An ambulatory monitoring system, comprising one or more ambulatory monitoring devices according to claim 1, wherein the ambulatory monitoring devices comprise a memory used for storing programs and a processor used for executing the method according to claim 1.

9. A computer readable storage medium, comprising instructions, wherein when the instructions run on a computer, the computer executes the method according to claim 1.

10. An ambulatory monitoring system, comprising the server according to claim 5 and one or more ambulatory monitoring devices, wherein the server comprises a memory used for storing programs and a processor used for executing the method according to claim 5.

11. A computer readable storage medium, comprising instructions, wherein when the instructions run on a computer, the computer executes the method according to claim 5.

* * * * *